United States Patent
Lagrange

(10) Patent No.: US 7,419,511 B2
(45) Date of Patent: Sep. 2, 2008

(54) COMPOSITIONS COMPRISING AT LEAST ONE SUBSTITUTED CARBOCYANIN DERIVATIVE, PROCESSES FOR TREATING KERATIN FIBERS USING THEM, DEVICE THEREFOR AND USES THEREOF

(75) Inventor: Alain Lagrange, Coupvray (FR)

(73) Assignee: L'Oreal, S.A., Paris (FR)

( * ) Notice: Subject to any disclaimer, the term of this patent is extended or adjusted under 35 U.S.C. 154(b) by 247 days.

(21) Appl. No.: 11/223,961

(22) Filed: Sep. 13, 2005

(65) Prior Publication Data

US 2006/0090269 A1   May 4, 2006

Related U.S. Application Data

(60) Provisional application No. 60/616,406, filed on Oct. 7, 2004.

(30) Foreign Application Priority Data

Sep. 13, 2004   (FR)   ................... 04 09695

(51) Int. Cl.
*A61Q 5/10* (2006.01)
*C07D 235/00* (2006.01)
(52) U.S. Cl. ............ 8/405; 8/406; 8/407; 8/409; 8/416; 8/431; 8/565; 8/571; 8/575; 8/576; 544/235
(58) Field of Classification Search ............ 8/405, 8/406, 407, 409, 416, 431, 565, 571, 575, 8/576; 544/235
See application file for complete search history.

(56) References Cited

U.S. PATENT DOCUMENTS

| | | | |
|---|---|---|---|
| 2,528,378 A | 10/1950 | Mannheimer |
| 2,781,354 A | 2/1957 | Mannheimer |
| 2,798,053 A | 7/1957 | Brown |
| 2,923,692 A | 2/1960 | Ackerman et al. |
| 3,666,464 A | 5/1972 | Keller et al. |
| 3,679,427 A | 7/1972 | Lincoln et al. |
| 3,821,233 A | 6/1974 | Lincoln et al. |
| 3,864,644 A | 2/1975 | Lincoln et al. |
| 3,904,637 A | 9/1975 | Lincoln et al. |
| 3,915,921 A | 10/1975 | Schlatzer, Jr. |
| 4,011,086 A | 3/1977 | Simson |
| 4,237,243 A | 12/1980 | Quack et al. |
| 4,309,551 A | 1/1982 | Schönberger et al. |
| 4,509,949 A | 4/1985 | Huang et al. |
| 4,823,985 A | 4/1989 | Grollier et al. |
| 5,089,578 A | 2/1992 | Valint et al. |
| 5,474,578 A | 12/1995 | Chan et al. |
| 5,708,151 A | 1/1998 | Möckli |
| 5,733,343 A | 3/1998 | Möckli |
| 5,734,058 A | 3/1998 | Lee |
| 5,792,221 A | 8/1998 | Lagrange et al. |
| 5,830,446 A | 11/1998 | Berthiaume et al. |
| 5,914,373 A | 6/1999 | Glancy et al. |
| 5,981,747 A | 11/1999 | Mujumdar et al. |
| 5,986,093 A | 11/1999 | Mujumdar et al. |
| 6,120,780 A | 9/2000 | Dupuis et al. |
| 6,133,445 A | 10/2000 | Waggoner et al. |
| 6,228,129 B1 | 5/2001 | De La Mettrie et al. |
| 6,686,145 B1 | 2/2004 | Waggoner et al. |
| 6,783,559 B2 | 8/2004 | De La Mettrie et al. |
| 6,822,039 B1 | 11/2004 | Monfreux-Gaillard et al. |
| 2002/0010967 A1 | 1/2002 | De La Mettrie et al. |
| 2003/0009833 A9 | 1/2003 | De La Mettrie et al. |
| 2003/0124079 A1 | 7/2003 | Mougin et al. |
| 2003/0188390 A1 | 10/2003 | Matsunaga |
| 2003/0224391 A1 | 12/2003 | Waggoner et al. |
| 2004/0078906 A1 | 4/2004 | Plos et al. |
| 2004/0088798 A1 | 5/2004 | Lang |
| 2004/0205901 A1 | 10/2004 | Cottard et al. |
| 2005/0028301 A1 | 2/2005 | Pastore |
| 2005/0144741 A1 | 7/2005 | Lang et al. |
| 2006/0010617 A1 | 1/2006 | Gourlaouen et al. |
| 2006/0117497 A1 | 6/2006 | Lang et al. |
| 2007/0039107 A1 | 2/2007 | Lang et al. |

FOREIGN PATENT DOCUMENTS

| | | |
|---|---|---|
| DE | 38 29 870 | 4/1989 |
| DE | 197 32 016 | 1/1999 |
| EP | 0 121 326 | 10/1984 |
| EP | 0 173 109 B1 | 10/1989 |
| EP | 0 395 282 B1 | 3/1995 |
| EP | 0 503 853 B1 | 5/1996 |
| EP | 0 747 448 | 12/1996 |
| EP | 0 750 899 A2 | 1/1997 |
| EP | 0 815 828 B1 | 2/1999 |
| EP | 1 166 753 | 1/2001 |
| EP | 1 166 757 | 1/2001 |
| EP | 1 133 978 | 9/2001 |
| EP | 1 170 001 | 1/2002 |
| EP | 0 714 954 B1 | 9/2002 |
| EP | 1 352 632 | 10/2003 |
| EP | 1 415 643 A1 | 5/2004 |
| EP | 1 634 575 | 3/2006 |
| EP | 1 652 553 | 5/2006 |

(Continued)

OTHER PUBLICATIONS

English abstract of the JP Patent No. 80012407.*

(Continued)

*Primary Examiner*—Eisa B Elhilo
(74) *Attorney, Agent, or Firm*—Finnegan, Henderson, Farabow, Garrett & Dunner LLP

(57) ABSTRACT

The disclosure provides compositions comprising, in a cosmetically acceptable medium, at least one direct dye, processes for treating keratin fibers, such as human keratin fibers, using the compositions, and devices comprising the compositions. Use of the compositions as lightening agents and as coloring agents for the keratin fibers is also provided.

48 Claims, No Drawings

FOREIGN PATENT DOCUMENTS

| | | |
|---|---|---|
| EP | 1 652 554 | 5/2006 |
| FR | 1 573 139 | 7/1969 |
| FR | 2 416 723 A1 | 9/1979 |
| FR | 2 586 913 A1 | 3/1987 |
| FR | 2 692 572 A1 | 12/1993 |
| FR | 2 741 261 | 5/1997 |
| FR | 2 811 993 A1 | 1/2002 |
| FR | 2 820 032 A1 | 8/2002 |
| FR | 2 875 130 | 3/2006 |
| FR | 2 875 131 | 3/2006 |
| FR | 2 875 132 | 3/2006 |
| GB | 1 529 807 | 10/1978 |
| JP | A 2000-86472 | 3/2000 |
| JP | T 2000-507986 | 6/2000 |
| JP | T 2000-507987 | 6/2000 |
| JP | A- 2001-261534 | 9/2001 |
| JP | T 2002-508428 | 3/2002 |
| JP | T 2003-528054 | 9/2003 |
| JP | A 2004-210778 | 7/2004 |
| JP | 2006-083170 | 3/2006 |
| WO | WO 95/01772 A1 | 1/1995 |
| WO | WO 95/15144 A1 | 6/1995 |
| WO | WO 97/17471 | 5/1997 |
| WO | WO 99/13849 | 3/1999 |
| WO | WO 99/31181 | 6/1999 |
| WO | WO 00/31154 A1 | 6/2000 |
| WO | WO 00/68282 A1 | 11/2000 |
| WO | WO 03/028685 A1 | 4/2003 |

OTHER PUBLICATIONS

STIC Search Report dated Jun. 6, 2007.*
C.J. Tredwell et al. Chemical Physics 43 (1979).*
Eaves, J. et al., "An MNDO study of dipyridopyrazinium and relation cations: instability of certain fused heteroaromic dications with two bridgehead nitrogens" *Can. J. Chem.* 64:1711-13 (1986).
Fonnum, G. et al., "Associative thickeners. Part I: Synthesis, rheology and aggregation behavior," *Colloid Polym. Sci.* 271(4):380-89 (1993).
Morishima, Y., "Self-assembling amphiphilic polyelectrolytes and their nanostructures," *Chinese J. Polymer Science* 18(40):323-36 (2000).
Noda, T. et al., "Micelle formation of random copolymers of sodium 2-(acrylamido)-2-methylpropanesulfonate and a nonionic surfactant macromonomer in water as studied by fluorescence and dynamic light scattering," *Macromolecules* 33(10):3694-3704 (2000).
Noda, T. et al., "Solution properties of micelle networks formed by nonionic surfactant moieties covalently bound to a polyelectrolyte: salt effects on rheological behavior," *Langmuir* 16(12):5324-32 (2000).
Noda, T. et al., "Stimuli responsive amphiphilic copolymers of sodium 2-(acrylamido)-2-methylpropanesulfonate and associative macromonomers," *Polymer Preprints* 40(2):220-221 (1999).
Tredwell, C. et al., "Picosecond time resolved fluorescence lifetimes of the polymethine and related dyes," *Chem. Phys.* 43(3):307-16 (1979).
Zviak, C., *The Science of Hair Care*, Masson, Paris, pp. 215, 278 (1988).
Yarmolyuk, S.M. "Interaction of Cyanine Dyes with Nucleic Acids: Investigation of Cyanine Dyes as Fluorescent Probes for the Nucleic Acids Detection," *Biopolimeriy / Kletka*, 15 (4):328-336 (1999).
Romanov, N.N. et al., "Cyanine Dyes with three cyclic groupings of dihydrooxazino- and dihydrothiazinobenzothiasolium salts," Dopovidi Akademii Nauk Ukrains'Koi RSR, Seriya B: Geologichni, Khimichni Ta Biologichni Nauki, (7), 622-4 (1976).
Porter, M.R. "Handbook of Surfactants," Blackie & Son, LTD., pp. 116-178 (1991).
Co-pending U.S. Appl. No. 11/223,962, filed Sep. 13, 2005.
Co-pending U.S. Appl. No. 11/223,149, filed Sep. 12, 2005.
French Search Report for French Appln. No. 04/09694, related to co-pending U.S. Appl. No. 11/223,962, 2005.
French Search Report for French Appln. No. 04/09693, related to co-pending U.S. Appl. No. 11/223,962, 2005.
French Search Report for French Appln. No. 04/09695, related to present U.S. Appl. No. 11/223,961, 2005.
Babichev, F.S. et al., "Cyanine Dyes from Dihydrooxazino- and Dihydrothiazino- Bennzthiazolium Salts," translated from *Zhurnal Organicheskoi Khimii*, vol. 1, No. 3, pp. 556-561, Mar. 1965.
Babichev, F.S. et al., "Styryl Dyes, Mero- and Rhodacyanine from 2,3-Polymethylenebenzothiazolium Salts," translated from *Zhurnal Obshehei Khimii*, vol. 34, No. 7, pp. 2447-2454, Jul. 1964.
English-language Derwent Abstract for JP-A- 2001-261534, Sep. 2001.
Daltrozzo, E et al., "Tautomerism of Quinoline Red Dyes," Abstract from *Chimia*, 1965, 19(15), pp. 325-332.
Office Action dated Oct. 10, 2007, co-pending U.S. Appl. No. 11/223,149.
Notice of Allowance and Fees Due dated Jan. 9, 2008, co-pending U.S. Appl. No. 11/223,149.
STIC Search Report dated Jun. 5, 2007, co-pending U.S. Appl. No. 11/223,149.
Office Action dated Oct. 23, 2007, co-pending U.S. Appl. No. 11/223,962.
Notice of Allowance and Fees Due dated Jan. 9, 2008, co-pending U.S. Appl. No. 11/223,962.
STIC Search Report dated Jun. 6, 2007, co-pending U.S. Appl. No. 11/223,962.
English-language Derwent abstract for DE 38 29 870, Apr. 1989.
English-language Derwent abstract for DE 197 32 016, Jan. 1999.
Notice of Allowance and Fees Due dated Apr. 17, 2008, co-pending U.S. Appl. No. 11/223,149.
Notice of Allowance and Fees Due dated Apr. 18, 2008, co-pending U.S. Appl. No. 11/223,962.

* cited by examiner

COMPOSITIONS COMPRISING AT LEAST ONE SUBSTITUTED CARBOCYANIN DERIVATIVE, PROCESSES FOR TREATING KERATIN FIBERS USING THEM, DEVICE THEREFOR AND USES THEREOF

CROSS-REFERENCE TO RELATED APPLICATIONS

This application claims benefit of U.S. Provisional Application No. 60/616,406, filed Oct. 7, 2004, the contents of which are incorporated herein by reference. This application also claims benefit of priority under 35 U.S.C. § 119 to French Patent Application No. 04 09 695, filed Sep. 13, 2004, the contents of which are also incorporated by reference.

FIELD OF THE INVENTION

The disclosure provides compositions comprising, in a cosmetically acceptable medium, at least one direct dye. The disclosure also provides processes for treating keratin fibers using the compositions, and devices comprising them. Additionally, the disclosure provides uses of the compositions as lightening agents and as coloring agents for fibers.

The present disclosure relates to the field of dyeing keratin fibers including dyeing the hair.

BACKGROUND OF THE INVENTION

There are generally two types of dyeing. The first type is semi-permanent dyeing or direct dyeing, which involves dyes capable of giving the hair's natural color a pronounced change. The dyes used are colored and coloring substances that have an affinity for keratin fibers. This type of dyeing fades out after several washes, which may be an inconvenience.

When it is desired to obtain a coloration that is lighter than the original color of the fibers, it is necessary to use, with the direct dyes, at least one oxidizing agent, under alkaline pH conditions. However, these conditions have consequences on the properties of the treated fibers. With time, the fibers become degraded and have a tendency to become coarse, dull, brittle, and difficult to style.

The second type is permanent dyeing or oxidation dyeing. This dyeing is performed with oxidation dye precursors, which are colorless or weakly colored compounds, comprising at least one oxidation base optionally combined with one or more couplers. Once mixed with oxidizing products, at the time of use, the precursors may give rise to colored compounds and dyes via a process of oxidative condensation.

Given the necessary presence of an oxidizing agent in this type of dyeing, the drawbacks mentioned above also occur in this case.

It has recently been found that compositions comprising at least one fluorescent compound represent an advantageous alternative to standard processes using an oxidizing agent. Thus, for dark hair, such as hair with a tone height of less than or equal to 6 (dark blond), such as less than or equal to 4 (chestnut-brown), it can be seen that there are regions for which the curve of reflectance as a function of the wavelength (from 500 to 700 nm) of hair treated with the composition comprising the fluorescent compound is higher than the curve corresponding to untreated hair. Consequently, the hair appears lighter, without the use of an oxidizing agent.

The term "tone" is based on the classification of the natural shades, one tone separating each shade from the shade immediately following or preceding it. This definition and the classification of the natural shades are well known to hairstyling professionals and are published in the book "Sciences des traitements capillaires [Hair treatment sciences]" by Charles Zviak, 1988, published by Masson, pp. 215 and 278. The tone heights range from 1 (black) to 10 (light light blond), one unit corresponding to one tone; the higher the figure, the lighter the shade.

Although such fluorescent compound containing compositions are an advancement in the field, they suffer from the drawbacks of instability upon storage.

Moreover, it would also be desirable to further increase the wash-fastness and shampoo-fastness of the colorations obtained using these compositions.

DETAILED DESCRIPTION OF THE INVENTION

It has been found, entirely unexpectedly, that compositions comprising at least one direct dye compound make it possible to obtain colorations with improved properties, in terms of fastness and selectivity (difference in coloration between the various parts of a hair or of a head of hair) and also showing improved stability of the composition. These properties are useful for fluorescent compounds in the context of lightening without the need to use an oxidizing agent.

In one aspect, the present disclosure provides compositions comprising, in a cosmetically acceptable medium, at least one direct dye of formula (I) or (I') below:

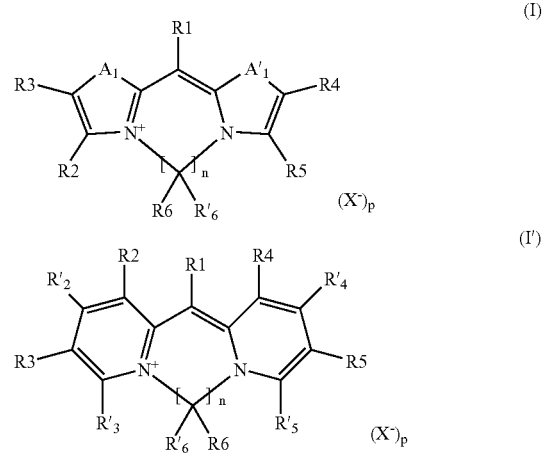

wherein:
$A_1$ and $A'_1$, which may be identical or different, are each chosen from oxygen, sulfur, and nitrogen substituted with a linear or branched $C_1$-$C_6$ alkyl radical, optionally substituted with one or more groups chosen from halo, hydroxyl; selenium, and $CR'_2$;

$R_1$, $R_6$ and $R'_6$, which may be identical or different, are each chosen from hydrogen; a linear, branched or cycloalkyl $C_1$-$C_{22}$ radical (such as a $C_1$-$C_6$ alkyl radical), optionally substituted with at least one hydroxyl group, at least one linear or branched $C_1$-$C_6$ alkoxy group, at least one $C_1$-$C_6$ cycloalkoxy group, or at least one $C_6$-$C_{30}$ aryl or an aryloxy group optionally substituted with at least one sulfo group, at least one carboxyl group or at least one $C_1$-$C_6$ alkoxycarbonyl group; and a $C_6$-$C_{30}$ aryl radical;

$R_2$, $R'_2$, $R_3$, $R'_3$, $R_4$, $R'_4$, $R_5$ and $R'_5$, which may be identical or different, are each chosen from hydrogen; a linear or branched $C_1$-$C_{22}$ radical (such as $C_1$-$C_{10}$ and $C_1$-$C_6$ alkyl radicals) optionally substituted with at least one hydroxyl, carboxyl, halo or sulfo radical; or $R_2, R'_2, R_3$ and $R'_3$, may optionally form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, with at least one halogen atom, at least one sulfo radical, at least one carboxyl group, or at least one $C_6$-$C_{30}$ aryl radical;

$R_4, R'_4, R_5$ and $R'_5$, may optionally form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, at least one halogen atom, at least one sulfo radical, at least one carboxyl group, or at least one $C_6$-$C_{30}$ aryl radical;

$R_2$ and $R_6$, $R_5$ and $R_6$, $R'_3$ and $R_6$ and/or $R'_5$ and $R_6$ may optionally form a heteroaromatic ring;

or in formula (I'), $R_2$ and $R'_2$, $R_3$ and $R'_3$, $R_2$ and $R'_4$ and/or $R_5$ and $R'_5$ may form in pairs with the carbon atoms to which each is attached, an aromatic or heteroaromatic ring;

n is an integer ranging from 1 to 3;

p is an integer equal to 0 or 1; and $X^-$ is an organic or mineral anion.

The present disclosure also provides processes for treating keratin fibers, including human keratin fibers, in which the compositions are applied to wet or dry fibers, for a time sufficient to develop the coloration, after which the fibers are rinsed, optionally washed with shampoo, rinsed again and dried, or the resulting fibers are left to dry.

In some embodiments of the processes, the compositions are applied to the wet or dry fibers without final rinsing.

The present disclosure also provides devices comprising the compositions.

Additionally, the present disclosure provides uses of the compositions as agents for lightening keratin fibers and/or as agents for dyeing these fibers.

Other characteristics and advantages of the invention will emerge more clearly on reading the description and the examples that follow.

In the text hereinbelow, and unless otherwise indicated, the limits of a range of values are understood as forming part of that range.

The compositions described herein make it possible to obtain colorations that are lighter than the original color of the keratin fibers, when it is applied onto dark fibers, without the presence of an oxidizing agents. However, oxidizing agents are not excluded from the compositions; i.e., the compositions may comprise oxidizing agents.

As used herein, the term "human keratin fibers" encompasses the hair, the eyelashes and the eyebrows.

The compositions are suitable for treating keratin fibers, irrespective of their coloration before treatment and whether or not their coloration is natural or artificially obtained.

In some embodiments, the compositions are formulated to be applied to dark keratin fibers. For example, the dark keratin fibers are pigmented or artificially dyed fibers, the tone height of which is less than or equal to 6, such as less than or equal to 4.

As indicated above, the direct dye is of formula (I) or (I') below:

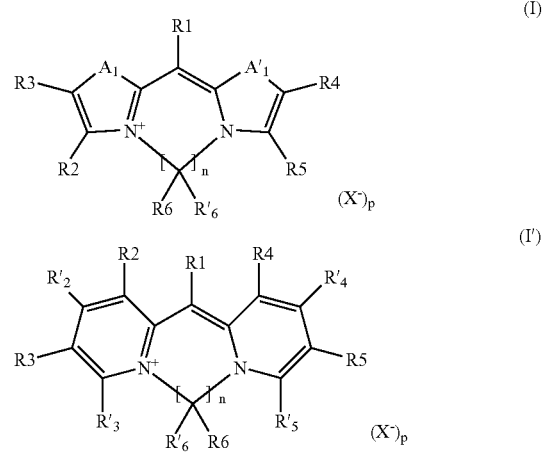

wherein:

$A_1$ and $A'_1$, which may be identical or different, are each chosen from oxygen, sulfur, and nitrogen substituted with a linear or branched $C_1$-$C_6$ alkyl radical, optionally substituted with one or more groups chosen from halo, hydroxyl; selenium, and $CR'_2$;

$R_1, R_6$ and $R'_6$, which may be identical or different, are each chosen from hydrogen; a linear, branched or cycloalkyl $C_1$-$C_{22}$ radical (such as a $C_1$-$C_6$ alkyl radical), optionally substituted with at least one hydroxyl group, at least one linear or branched $C_1$-$C_6$ alkoxy group, at least one $C_1$-$C_6$ cycloalkoxy group, or at least one $C_6$-$C_{30}$ aryl or an aryloxy group optionally substituted with at least one sulfo group, at least one carboxyl group or at least one $C_1$-$C_6$ alkoxycarbonyl group; and a $C_6$-$C_{30}$ aryl radical;

$R_2, R'_2, R_3, R'_3, R_4, R'_4, R_5$ and $R'_5$, which may be identical or different, are each chosen from hydrogen; a linear or branched $C_1$-$C_{22}$ radical (such as $C_1$-$C_{10}$ and $C_1$-$C_6$ alkyl radicals) optionally substituted with at least one hydroxyl, carboxyl, halo or sulfo radical; or $R_2, R'_2, R_3$ and $R'_3$, may optionally form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, at least one halogen atom, at least one sulfo radical, at least one carboxyl group, or at least one $C_6$-$C_{30}$ aryl radical;

$R_4, R'_4, R_5$ and $R'_5$, may optionally form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, at least one halogen atom, at least one sulfo radical, at least one carboxyl group, or at least one $C_6$-$C_{30}$ aryl radical;

$R_2$ and $R_6$, $R_5$ and $R_6$, $R'_3$ and $R_6$ and/or $R'_5$ and $R_6$ may optionally form a heteroaromatic ring;

or in formula (I'), $R_2$ and $R'_2$, $R_3$ and $R'_3$, $R_2$ and $R'_4$ and/or $R_5$ and $R'_5$ may form in pairs with the carbon atoms to which each is attached, an aromatic or heteroaromatic ring;

n is an integer ranging from 1 to 3;
p is an integer equal to 0 or 1; and
$X^-$ is an organic or mineral anion.

The mesomeric forms of the compounds of formula (I) and (I') may also be used.

The direct dyes used in the compositions may be fluorescent molecules, i.e. molecule that color by themselves, are soluble in the medium, and absorb light of the visible spectrum and optionally of the ultraviolet spectrum (wavelengths ranging from 360 to 760 nm), but which, unlike a standard dye, converts a portion of the absorbed energy into fluorescent light of longer wavelength than that of the absorbed light, emitted in the visible part of the spectrum.

In addition, the fluorescent dyes are dyes that generate fluorescence on the support onto which they are applied.

The direct dyes may be soluble in the media of the compositions to at least 1 g per liter, for example to at least 5 g per liter, at a temperature of 25° C.

In some embodiments, the radicals $R_1$, $R_6$ and $R'_6$, are each chosen from hydrogen atoms; a linear or branched $C_1$-$C_{22}$ alkyl radical (for example, $C_1$-$C_6$), optionally substituted with at least one phenyl or phenyloxy group optionally substituted with at least one sulfo group, at least one carboxyl group, or at least one $C_1$-$C_6$ alkoxycarbonyl group; or a phenyl radical.

In some embodiments, $R'_6$ is a hydrogen atom.

In some embodiments, $R_2$, $R'_2$, $R_3$ and $R'_3$ or $R_4$, $R'_4$, $R_5$ and $R'_5$ form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring being optionally substituted with at least one linear or branched $C_1$-$C_6$ alkyl radical optionally bearing a carboxyl group, with at least one halogen atom, at least one sulfo radical, or at least one carboxyl group.

In other embodiments, at least one of the radicals $R_2$, $R'_2$, $R_3$, $R'_3$, $R_4$, $R'_4$, $R_5$ and $R'_5$ is chosen from hydrogen, a linear or branched $C_1$-$C_{22}$ alkyl radical, such as a $C_1$-$C_{10}$ or $C_1$-$C_6$ alkyl radical.

In some of these embodiments, at least one of the radicals $R_2$, $R'_2$, $R_3$, $R'_3$, $R_4$, $R'_4$, $R_5$ and $R'_5$ is a hydrogen atom or a methyl radical.

In some embodiments, $A_1$ is identical to $A'_1$.

In some embodiments, $X^-$ is an anion of mineral origin, for example, chosen from halides, sulfates, bisulfates, nitrates, phosphates, hydrogen phosphates, dihydrogen phosphates, carbonates, and bicarbonates.

In other embodiments, $X^-$ is an anion of organic origin, for example, chosen from anions originating from salts of saturated or unsaturated, aromatic or non-aromatic sulfuric, sulfonic, mono- or polycarboxylic acids, optionally substituted with at least one hydroxyl or amino radical or halogen atoms.

In certain embodiments, $X^-$ is chosen from chloride, iodide, sulfate, methosulfate and ethosulfate.

In some embodiments, the direct dyes are chosen from one of the following compounds:

internal salt of bisnaphtho[2', 3':4, 5]thiazolo[3, 2-d:2', 3'-g][1, 4]diazepin-15-ium, 16, 17-dihydro-16, 17-bis[2-(2-sulfophenyl)ethyl]

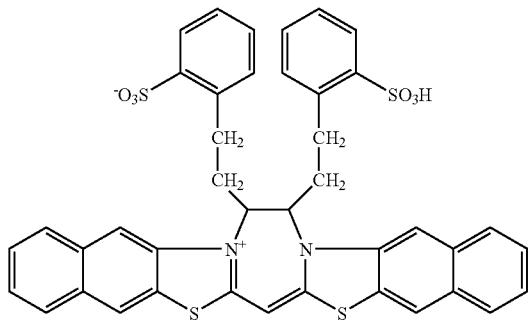

Salt (for example chloride) of bisnaphtho[2', 3':4, 5]thiazolo[3, 2-d:2', 3'-g][1, 4]diazepin-15-ium, 16, 17-dihydro-16, 17-bis(3-phenoxypropyl)-

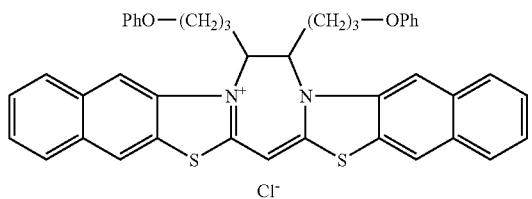

Salt (for example chloride) of bisbenzothiazolo[3, 2-d:2', 3'-g][1, 4]diazepin-12-ium, 13, 14-dihydro-2, 10, 13, 14-tetraphenyl

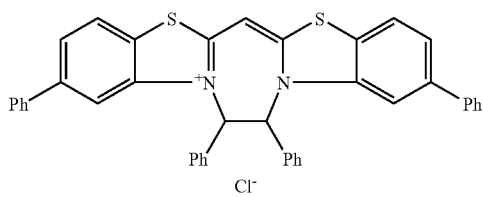

-continued

| | |
|---|---|
| Bisnaphth[2', 3':4, 5]oxazolo[3, 2-d:2', 3'-g][1, 4]diazepin-15-ium, 16, 17-dihydro-, chloride | 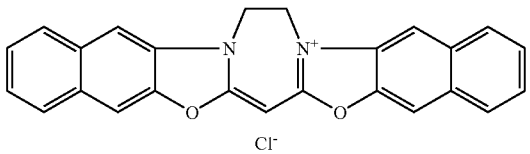 |
| Internal salt of bisbenzothiazolo[3, 2-d:2', 3'-g][1, 4]diazepin-12-ium, 13-(carboxymethyl)-13, 14-dihydro | 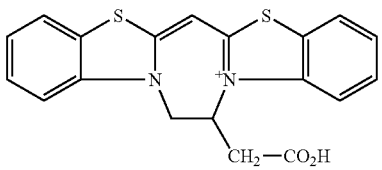 |
| Internal salt of bisbenzoxazolo[3, 2-d:2', 3'-g][1, 4]diazepin-12-ium, 13-(carboxymethyl)-13, 14-dihydro-2, 10-disulfo | 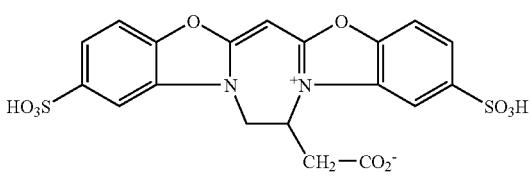 |
| Internal salt of bisbenzothiazolo[3, 2-d:2', 3'-g][1, 4]diazepin-12-ium, 13-(carboxymethyl)-13, 14-dihydro-2, 10-disulfo | 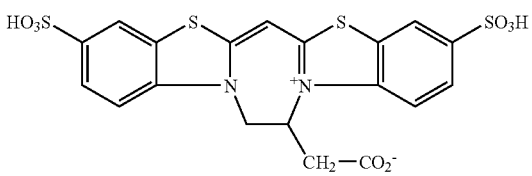 |
| Internal salt of bisbenzoxazolo[3, 2-d:2', 3'-g][1, 4]diazepin-12-ium, 13, 14-dihydro-13-(2-methoxy-2-oxoethyl)-2, 10-disulfo | 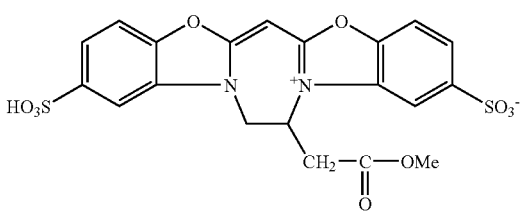 |
| Internal salt of benzothiazolo[3', 2':4, 5]-[1, 4]diazepino[7, 1-b]benzoxazol-12-ium, 2-(carboxymethyl)-13, 14-dihydro | 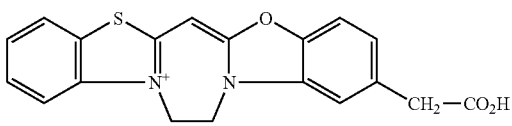 |
| Internal salt of bisbenzothiazolo[3, 2-d:2', 3'-g][1, 4]diazepin-12-ium, 6-(5-carboxypentyl)-13, 14-dihydro | 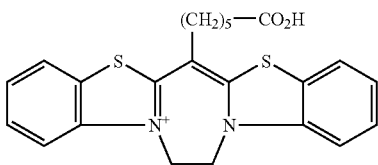 |
| Internal salt of benzothiazolo[3', 2':4, 5][1, 4]diazepino[7, 1-b]benzoxazol-12-ium, 2-carboxy-13, 14-dihydro-3, 9-disulfo | 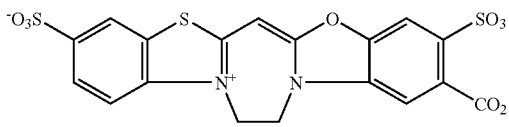 |
| 1, 4-Dihydrobisbenzothiazolo[3, 2-d:2', 3'-g][1, 4]diazepin-12-ium, iodide | 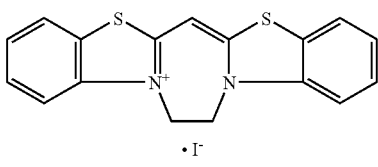 |

| | |
|---|---|
| 5H-Bisbenzimidazo[1, 2-d:2', 1'-g][1, 4]diazepinium, 2, 3, 9, 10-tetrachloro-5, 7-diethyl-13, 14-dihydro-, iodide | 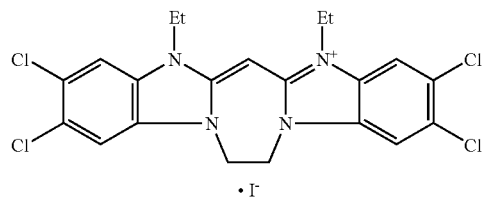 |
| 5H-Bisbenzimidazo[1, 2-d:2', 1'-g][1, 4]diazepinium, 2, 3, 9, 10-tetrachloro-13, 14-dihydro-5, 7-bis(2, 2, 2-trifluoroethyl)-, tosylate | 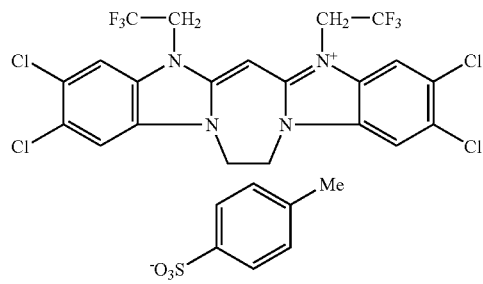 |
| 5H-Bisbenzimidazo[1, 2-d:2', 1'-g][1, 4]diazepinium, 2, 3, 9, 10-tetrachloro-13, 14-dihydro-5, 7-dimethyl, iodide | 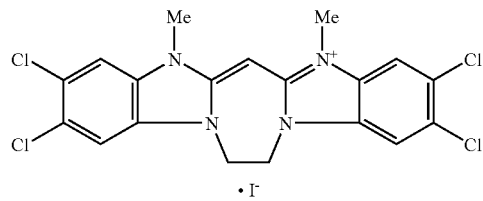 |
| 6H-[1, 4]Diazepino-[1'', 7'':1, 2; 4'', 5'':1', 2']diimidazo[4, 5-b:4', 5'-b']diquinoxalinium, 6, 8-diethyl-16, 17-dihydro, perchlorate | 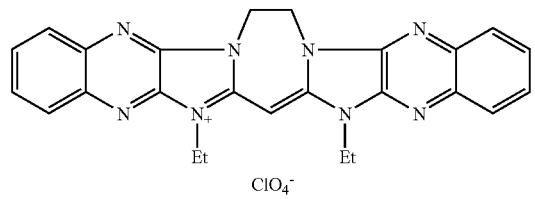 |
| 5H-Bisbenzimidazo[1, 2-d:2', 1'-g][1, 4]diazepinium, 5, 7-diethyl-13, 14-dihydro, iodide | 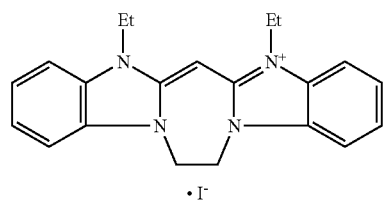 |
| Salt (for example chloride) of bisbenzimidazo[1, 2-d:2', 1'-g][1, 4]diazepin-12-ium, 5, 7, 13, 14-tetrahydro-5, 7-dimethyl | 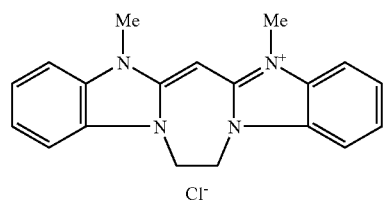 |
| Salt (for example chloride) of [1, 4]diazepino[7, 1, 2-cd:5, 4, 3-c'd']diindolizin-12-ium, 4, 5, 7, 8-tetramethyl | 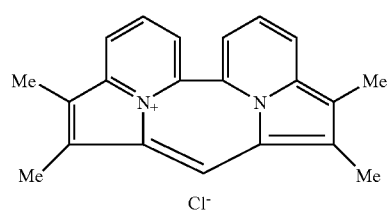 |

-continued

| | |
|---|---|
| Salt (for example chloride) of [1, 4]diazepino[7, 1, 2-cd:5, 4, 3-c'd']diindolizin-12-ium | 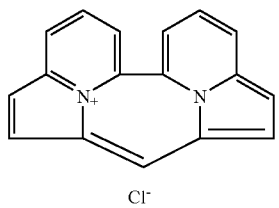 Cl⁻ |
| Salt (for example chloride) of bisbenzoxazolo[3, 2-d:2', 3'-g][1, 4]diazepin-12-ium, 13, 14-dihydro | 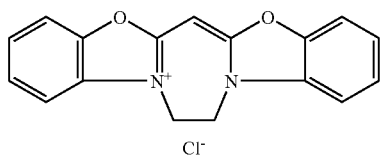 Cl⁻ |
| 10H-Pyrimido[1, 6-f:3, 4-f'] diphenanthridin-9-ium, iodide | 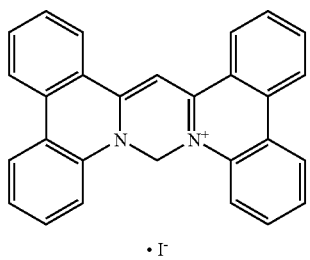 • I⁻ |
| 13H-Pyrido[1', 2':3, 4]pyrimido[1, 6-a]quinolin-14-ium, iodide | 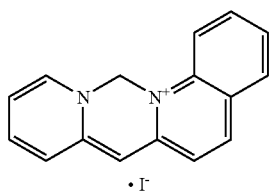 • I⁻ |
| 8H-Isoquino[2', 1':3, 4]pyrimido[1, 6-a]quinolin-7-ium 8-cyclohexyl, chloride | 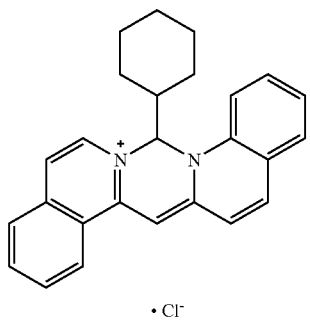 • Cl⁻ |
| 15H-Pyrimido[1, 6-a:3, 4-a']diquinolin-14-ium, iodide | 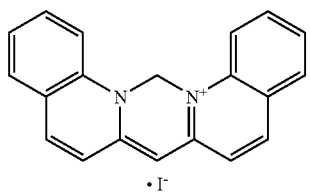 • I⁻ |
| 6H-Dipyrido[1, 2-c:2', 1'-f]pyrimidin-5-ium, iodide | 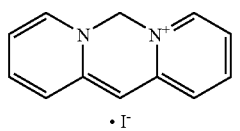 • I⁻ |

-continued
| | |
|---|---|
| Salt (for example chloride) of 17H-dibenzo[f, f']pyrimido[1, 6-a:3, 4-a']diquinolin-16-ium | 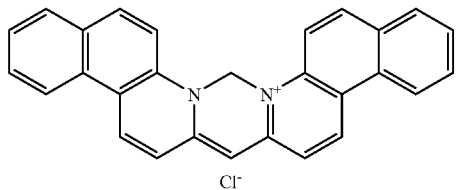 |
| 8H-Isoquino[2', 1':3, 4]pyrimido[1, 6-a]quinolin-7-ium, 8-phenyl-, chloride | 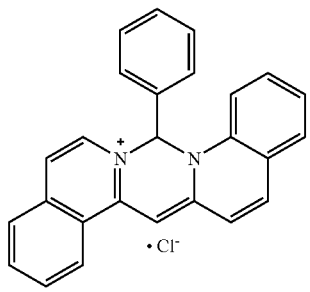 |
| 15-Phenyl-15H-pyrimido[1, 6-a:3, 4-a']diquinolin-14-ium, iodide | 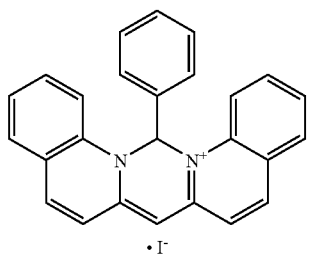 |
| 15H-Pyrimido[1, 6-a:3, 4-a']diquinolin-14-ium, 15, 15-diphenyl, chloride | 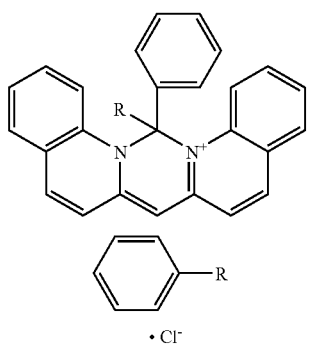 |
| 15H-Pyrimido[1, 6-a:3, 4-a']diquinolin-14-ium, chloride | 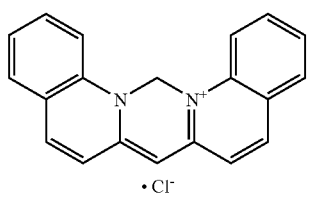 |
| Salt (for example chloride) of 13H-pyrimido[6, 1-b:4, 3-b']bisbenzothiazol-12-ium | 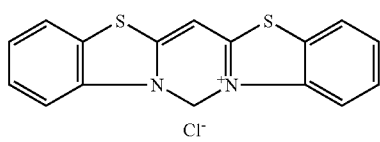 |

-continued

| | |
|---|---|
| 13H-Pyrimido[6, 1-b:4, 3-b']-bisbenzothiazol-12-ium, 6-phenyl-, iodide | 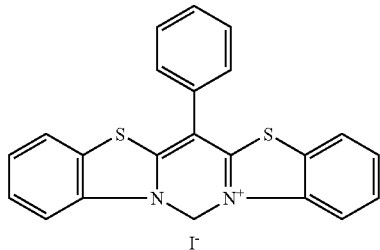 |
| 5H-Dipyrrolo[1, 2-c:2', 1'-f]pyrimidin-4-ium, 1, 3, 7, 9, 10-pentamethyl, chloride | 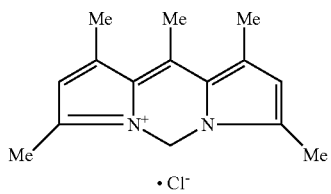 |
| Salt (for example chloride) of 5H-bisthiazolo[3, 2-c:2', 3'-f]pyrimidin-4-ium | 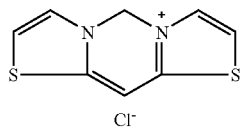 |
| 5H, 13H-Pyrimido[1, 6-a:3, 4-a']-bisbenzimidazolium, 2, 3, 9, 10-tetrachloro-5, 7-dimethyl, iodide | 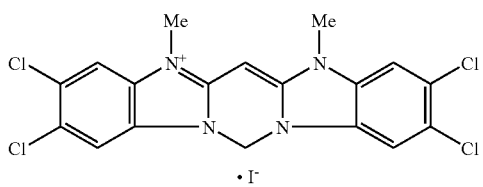 |
| 6H, 12H-Pyrimido[1, 6-a:3, 4-a']bisbenzimidazolium, 12, 14-dimethyl-, perchlorate | 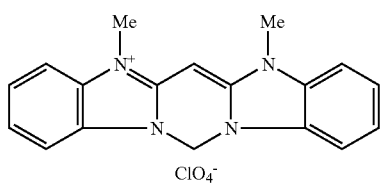 |
| Salt (for example chloride) of 6H, 12H-pyrimido[1, 6-a:3, 4-a']bisbenzimidazolium, 12, 14-dimethyl | 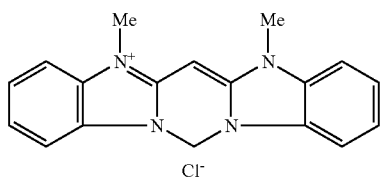 |
| Dipyrido[1, 2-d:2', 1'-g][1, 4]diazepin-5-ium, 6, 7-dihydro, bromide | 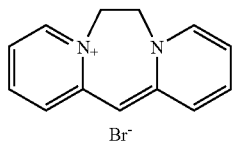 |
| Dipyrido[1, 2-d:2', 1'-g][1, 4]diazepin-5-ium, 6, 7-dihydro-2, 4, 9, 11-tetraphenyl, perchlorate | 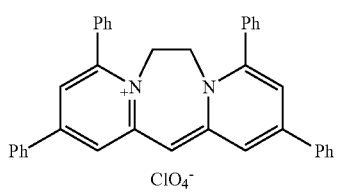 |

-continued

| | |
|---|---|
| Dipyrido[1, 2-d:2', 1'-g][1, 4]diazepin-5-ium, 2, 4, 9, 11-tetrakis(1, 1-dimethylethyl)-6, 7-dihydro, perchlorate | 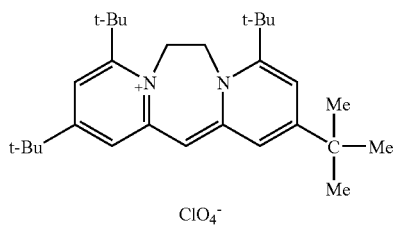 |
| [1, 4]Diazepino[1, 7-a:4, 5-a']diquinolin-14-ium, 15, 16-dihydro, bromide | 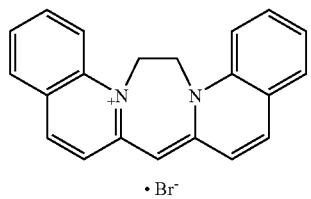 |
| 6H, 14H-Bisbenzimidazo[1, 2-a:2', 1'-d]-[1, 5]diazocinium, 2, 3, 11, 12-tetrachloro-7, 8-dihydro-14, 16-dimethyl, 4-methyl-benzenesulfonate | 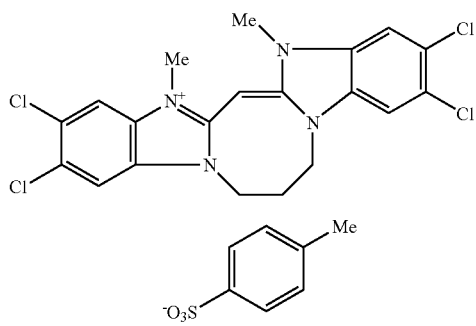 |
| Salt (for example chloride) of 6H-bisbenzothiazolo[3, 2-a:2', 3'-d][1, 5]-diazocin-5-ium, 7, 8-dihydro | 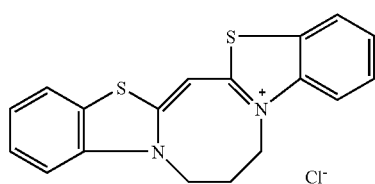 |

The nature of the counterion is not critical. Thus, the anions mentioned in the above table are given merely as examples.

The direct dye of formula (I) or (I') may represent from 0.01% to 20%, for example, from 0.1% to 5%, by weight relative to the total weight of the composition.

The cosmetically acceptable medium, may comprise water or a mixture of water and of at least one organic solvent.

Examples of organic solvents include, but are not limited to, $C_1$-$C_4$ linear or branched alkanols such as ethanol and isopropanol; glycerol; glycols and glycol ethers, for example, 2-butoxyethanol, propylene glycol, dipropylene glycol, propylene glycol monomethyl ether, diethylene glycol monomethyl ether and monoethyl ether; and aromatic alcohols, for example, benzyl alcohol or phenoxyethanol, similar products; and mixtures thereof.

The at least one solvent may be present in an amount ranging from approximately 1% to 40% by weight, for example from approximately 5% to 30% by weight, relative to the total weight of the dye composition.

The pH of the compositions generally ranges from approximately 3 to 12, for example, from 5 to 11. It may be adjusted to the desired value using acidifying or basifying agents known in the field of dyeing human keratin fibers.

Examples of acidifying agents that may be used include, but are not limited to, mineral and organic acids, for example, hydrochloric acid, orthophosphoric acid, sulfuric acid, carboxylic acids, for example, acetic acid, tartaric acid, citric acid and lactic acid, and sulfonic acids.

Examples of basifying agents that may be used include, but are not limited to, aqueous ammonia, alkaline carbonates, alkanolamines such as monoethanolamine, diethanolamine and triethanolamine and derivatives thereof, sodium hydroxide, potassium hydroxide and the compounds of formula (II) below:

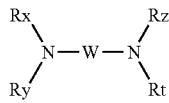

wherein W is a propylene residue optionally substituted with a hydroxyl group or a $C_1$-$C_6$ alkyl radical; $R_x$, $R_y$, $R_z$ and $R_t$, which may be identical or different, are each chosen from a hydrogen atom and a $C_1$-$C_6$ alkyl or $C_1$-$C_6$ hydroxyalkyl radical.

The cosmetic compositions may also comprise one or more additional nonionic, cationic or anionic-direct dyes (for example, cationic or nonionic), or combinations thereof.

Direct dyes include, but are not limited to, nitrobenzene, azo, azomethine, methine, anthraquinone, naphthoquinone, benzoquinone, phenothiazine, indigoid, xanthene, phenanthridine, phthalocyanin, triarylmethane-based dyes and natural dyes, alone or as mixtures.

For example, the direct dyes may be chosen from the following red and orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The compositions may also comprise, in addition to or instead of these nitrobenzene dyes, one or more additional direct dyes chosen from yellow, green-yellow, blue and violet nitrobenzene dyes, azo dyes, anthraquinone dyes, naphthoquinone dyes, benzoquinone dyes, indigoid dyes, and triarylmethane-based dyes.

These additional direct dyes may be basic dyes, for example, the dyes listed in the Color Index, 3rd edition, under the names "Basic Brown 16," "Basic Brown 17," "Basic Yellow 57," "Basic Red 76," "Basic Violet 10," "Basic Blue 26," and "Basic Blue 99," or acidic direct dyes, for example, the dyes listed in the Color Index, 3rd edition, under the names "Acid Orange 7," "Acid Orange 24," "Acid Yellow 36," "Acid Red 33," "Acid Red 184," "Acid Black 2," "Acid Violet 43" and "Acid Blue 62," or alternatively cationic direct dyes such as those described in WO 95/01772, WO 95/15144 and EP 714 954, each hereby incorporated by reference.

Yellow and green-yellow nitrobenzene direct dyes that may be used include, but are not limited to:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Blue and violet nitrobenzene direct dyes that may be used include, but are not limited to:
1-(β-hydroxyethyl)amino-4-N,N-bis(β-hydroxyethyl)amino-2-nitrobenzene,
1-(γ-hydroxypropyl)amino-4, N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene, and
2-nitro-para-phenylenediamines having the following formula:

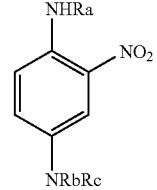

wherein:
  $R_b$ is chosen from $C_1$-$C_4$ alkyl radicals and β-hydroxyethyl, β-hydroxypropyl or γ-hydroxypropyl radicals;
  $R_a$ and $R_c$, which may be identical or different, are chosen from a β-hydroxyethyl, β-hydroxypropyl, γ-hydroxypropyl and β,γ-dihydroxypropyl radicals, at least one of the radicals $R_b$, $R_c$ or $R_a$ representing a γ-hydroxypropyl radical and $R_b$ and $R_c$ not simultaneously being able to denote a β-hydroxyethyl radical when $R_a$ is a γ-hydroxypropyl radical, such as those described in French patent FR 2 692 572.

Natural direct dyes include, but are not limited to, henna, camomile and indigo, inter alia.

The at least one additional direct dye may be present in amounts ranging from 0.0005% to 12% by weight, for example, 0.005% to 6% by weight, relative to the total weight of the composition.

When used for oxidation dyeing, the cosmetic compositions may further comprise at least one oxidation base chosen from the oxidation bases conventionally used for oxidation dyeing such as para-phenylenediamines, bis(phenyl)alkylenediamines, para-aminophenols, ortho-aminophenols, heterocyclic bases, and acid or alkaline addition salts thereof.

Para-phenylenediamines include, but are not limited to, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)- para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4'-aminophenyl-1-(3-hydroxy)pyrrolidine, and acid or alkaline addition salts thereof.

In some embodiments, the para-phenylenediamines used are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and and acid or alkaline addition salts thereof.

Bis(phenyl)alkylenediamines include, but are not limited to, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and acid or alkaline addition salts thereof.

Para-aminophenols include, but are not limited to, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid or alkaline addition salts thereof.

Ortho-aminophenols include, but are not limited to, 2-aminophenol, 2-amino-5-methylphenol, 2-amino-6-methylphenol, 5-acetamido-2-aminophenol, and acid or alkaline addition salts thereof.

Heterocyclic bases include, but are not limited to, pyridine derivatives, pyrimidine derivatives, pyrazole derivatives, and acid or alkaline addition salts thereof.

When used, the at least one oxidation base may be present in an amount ranging from 0.0005% to 12% by weight, for example, 0.005% to 6% by weight, relative to the total weight of the composition.

When intended for oxidation dyeing, the compositions may further comprise at least one coupler so as to modify or to enrich with glints the shades obtained using the direct dyes and the at least one oxidation base.

Couplers that may be used include couplers conventionally used in oxidation dyeing, and include, but are not limited to, meta-phenylenediamines, meta-aminophenols, meta-diphenols, heterocyclic couplers, and acid or alkaline addition salts thereof.

The at least one coupler may be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-di-hydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, and acid or alkaline addition salts thereof.

When present, the couplers may be from 0.0001% to 10% by weight, for example, from 0.005% to 5% by weight, relative to the total weight of the composition.

In general, the acid addition salts that may be used in the compositions (oxidation bases and couplers) are chosen from hydrochlorides, hydrobromides, sulfates, citrates, succinates, tartrates, tosylates, benzenesulfonates, lactates, and acetates.

Addition salts with an alkaline agent (oxidation bases and couplers) that may be used in the compositions include, but are not limited to, alkali and alkaline-earth metals addition salts, with ammonia and with organic amines, including alkanolamines and compounds of formula (II).

The cosmetic compositions may also comprise various adjuvants conventionally used in cosmetic compositions, for example, for dyeing human keratin fibers, such as anionic, cationic, nonionic, amphoteric and zwitterionic polymers, and mixtures thereof, mineral thickeners, antioxidants, penetrating agents, sequestering agents, fragrances, buffers, dispersants, conditioners, for instance cations, cationic and amphoteric polymers, chitosans, volatile and non-volatile, modified or unmodified silicones, film-forming agents, ceramides, preserving agents, stabilizers, and opacifiers.

The compositions may comprise one or more surfactants. These surfactants may be chosen from anionic, amphoteric, nonionic, zwitterionic and cationic surfactants, and mixtures thereof.

Suitable surfactants include, but are not limited to:

(i) Anionic Surfactants:

Anionic surfactants that may be used, alone or as mixtures, include, but are not limited to, salts (such as alkali metal salts, for example, sodium salts, ammonium salts, amine salts, amino alcohol salts, and magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$)alkyl sulfosuccinates, ($C_6$-$C_{24}$)alkyl ether sulfosuccinates, ($C_6$-$C_{24}$)alkylamide sulfosuccinates; ($C_6$-$C_{24}$)alkyl sulfoacetates; ($C_6$-$C_{24}$)acyl sarcosinates; and ($C_6$-$C_{24}$)acyl glutamates. ($C_6$-$C_{24}$)Alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates, the alkyl or acyl radical of all of these different compounds optionally having from 12 to 20 carbon atoms and the aryl radical optionally denoting a phenyl or benzyl group may also be used. Anionic surfactants which may also be used include, but are not limited to, fatty acid salts such as oleic, ricinoleic, palmitic and stearic acid salts, coconut oil acid or hydrogenated coconut oil acid; acyl lactylates in which the acyl radical has from 8 to 20 carbon atoms. It is also possible to use alkyl D-galactoside uronic acids and salts thereof, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and salts thereof, such as those having from 2 to 50 alkylene oxide groups, for example, ethylene oxide groups, and mixtures thereof.

(ii) Nonionic Surfactants:

Nonionic surfactants are known in the art. See, for example, "Handbook of Surfactants" by M. R. Porter, published by Blackie & Son (Glasgow and London), 1991, pp. 116-178 and their nature is not a critical factor. Thus, they may be chosen from, for example, polyethoxylated and polypropoxylated alkylphenols, alpha-diols and alcohols, having a fatty chain having, for example, from 8 to 18 carbon atoms. The number of ethylene oxide or propylene oxide groups may range from 2 to 50. Copolymers of ethylene oxide and of propylene oxide, condensates of ethylene oxide and of propylene oxide with fatty alcohols; polyethoxylated fatty amides, for example, having from 2 to 30 mol of ethylene oxide, polyglycerolated fatty amides having, for example, an average of 1 to 5 (e.g., 1.5 to 4) glycerol groups; polyethoxylated fatty amines optionally having from 2 to 30 moles of ethylene oxide; oxyethylenated fatty acid esters of sorbitan having from 2 to 30 moles of ethylene oxide; fatty acid esters of sucrose, fatty acid esters of polyethylene glycol, alkylpolyglycosides, N-alkylglucamine derivatives, and amine oxides such as ($C_{10}$-$C_{14}$)alkylamine oxides and N-acylaminopropylmorpholine oxides may also be used.

(iii) Amphoteric and Zwitterionic Surfactants:

Amphoteric and zwitterionic surfactants may be chosen from, for example, aliphatic secondary and tertiary amine derivatives in which the aliphatic radical is a linear or branched chain having from 8 to 18 carbon atoms and at least one water-solubilizing anionic group (for example, carboxylate, sulfonate, sulfate, phosphate or phosphonate). In some embodiments, ($C_8$-$C_{20}$)alkylbetaines, sulfobetaines, ($C_8$-$C_{20}$)alkylamido($C_1$-$C_6$)alkylbetaines, or ($C_8$-$C_{20}$)alkylamido($C_1$-$C_6$)alkylsulfobetaines are used.

Amine derivatives include, but are not limited to, the products sold under the name Miranol, as described in U.S. Pat. Nos. 2,528,378 and 2,781,354 and classified in the CTFA dictionary, 3rd edition, 1982, under the names amphocarboxyglycinates and amphocarboxypropionates, with the respective structures:

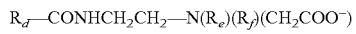

wherein:

$R_d$ is an alkyl radical of an acid $R_d$—COOH present in hydrolyzed coconut oil or a heptyl, nonyl or undecyl radical, $R_e$ is a beta-hydroxyethyl group and $R_f$ is a carboxymethyl group;

or

wherein:

B is —$CH_2CH_2OX$, C is —$(CH_2)_z$—Y, and z=1 or 2,

X is a —$CH_2CH_2$—COOH group or hydrogen,

Y is —COOH or a —$CH_2$—CHOH—$SO_3H$ radical, $R_g$ is an alkyl radical of an acid $R_g$—COOH present in coconut oil or in hydrolyzed linseed oil, a saturated radical, or a radical comprising one or more unsaturations, for example, a $C_7$ to $C_{17}$ (such as $C_9$, $C_{11}$, $C_{13}$ or $C_{17}$) alkyl radical or its iso form, or an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

For example, the cocoamphodiacetate sold under the trade name Miranol® $C_2M$ concentrate by the company Rhodia Chimie may be used.

(iv) Cationic Surfactants:

Cationic surfactants that may be used include, but are not limited to, salts of optionally polyoxyalkylenated primary, secondary, and tertiary fatty amines; quaternary ammonium salts such as tetraalkylammonium, alkylamidoalkyltrialkylammonium, trialkylbenzylammonium, trialkylhydroxyalkylammonium, and alkylpyridinium; chlorides and bromides; imidazoline derivatives; and cationic amine oxides.

In some embodiments, the surfactants are nonionic, anionic or amphoteric.

In some embodiments, the surfactants are present in an amount ranging from 0.01% to 50% by weight, for example, from 0.1% to 25% by weight, relative to the total weight of the composition.

The composition may also comprise one or more thickening polymers. These polymers may be ionic or nonionic, and associative or non-associative.

As used herein, non-associative thickening polymers means thickening polymers not containing a $C_{10}$-$C_{30}$ chain.

Non-associative thickening polymers, include, but are not limited to, crosslinked acrylic acid homopolymers, crosslinked 2-acrylamido-2-methylpropanesulfonic acid homopolymers and crosslinked acrylamide copolymers thereof, ammonium, acrylate homopolymers and copolymers of ammonium, acrylate and acrylamide, nonionic guar gums, microbial biopolysaccharide gums, plant exudate gums, hydroxypropyl- or carboxymethyl celluloses; pectins and alginates, alone or as mixtures.

In some embodiments, the non-associative thickening polymers are crosslinked acrylic acid homopolymers.

Homopolymers of this type, include, but are not limited to, those crosslinked with an allylic ether of an alcohol of a sugar, for example, the products sold under the names Carbopol 980, 981, 954, 2984 and 5984 by the company Noveon, and the products sold under the names Synthalen M and Synthalen K by the company 3 VSA.

The non-associative thickening polymers may also be chosen from crosslinked 2-acrylamido-2-methylpropanesulfonic acid homopolymers and crosslinked acrylamide copolymers thereof.

These homopolymers and copolymers may be partially or totally neutralized, and include polymers comprising from 90% to 99.9% by weight, relative to the total weight of polymer, of units of formula (j) below:

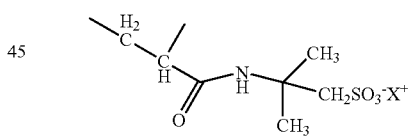

wherein $X^+$ denotes a cation, a mixture of cations, or a proton.

The cations may be chosen from alkali metals (for example, sodium and potassium), ammonium ions optionally substituted with from 1 to 3 alkyl radicals, which may be identical or different, having from 1 to 6 carbon atoms, optionally bearing at least one hydroxyl radical, cations derived from N-methylglucamine or from basic amino acids, for example, arginine and lysine. In some embodiments, the cation is an ammonium or sodium ion.

Moreover, the polymer may comprise from 0.01% to 10% by weight, relative to the total weight of the polymer, of crosslinking units derived from at least one monomer having at least two ethylenic unsaturations (i.e., carbon-carbon double bonds).

The crosslinking monomers having at least two ethylenic unsaturations may be chosen, for example, from diallyl ether, triallyl cyanurate, diallyl maleate, allyl (meth)acrylate, dipropylene glycol diallyl ether, polyglycol diallyl ethers, triethylene glycol divinyl ether, hydroquinone diallyl ether, tetraallyloxethanoyl, tetra- or diethylene glycol di(meth)acrylate, triallylamine, tetraallylethylenediamine, trimethylolpropanediallyl ether, trimethylolpropane triacrylate, methylenebis(meth)acrylamide or divinylbenzene, allylic ethers of alcohols of the sugars, other allylic or vinyl ethers of polyfunctional alcohols, allylic esters of phosphoric and/or vinylphosphonic acid, and mixtures of these compounds.

Details regarding these polymers can be found in EP 815 828.

Partially or totally neutralized crosslinked copolymers of 2-acrylamido-2-methylpropanesulfonic acid and of acrylamide include, for example, the product described in Example 1 of document EP 503 853.

The composition may also comprise, as non-associative thickening polymers, ammonium, acrylate homopolymers and copolymers of ammonium, acrylate and acrylamide.

Ammonium acrylate homopolymers include, for example, the product sold under the name Microsap PAS 5193 by the company Hoechst. Copolymers of ammonium, acrylate and of acrylamide include, for example, the product sold under the name Bozepol C Nouveau and the product PAS 5193 sold by the company Hoechst. A description and preparation of such compounds is disclosed in FR 2 416 723, and U.S. Pat. Nos. 2,798,053 and 2,923,692.

The composition may also comprise dimethylaminoethyl methacrylate homopolymers quaternized with methyl chloride or dimethylaminoethyl methacrylate copolymers quaternized with methyl chloride and acrylamide.

Homopolymers of this type include, for example, the products sold under the names Salcare 95 and Salcare 96 by the company Ciba-Allied Colloids. Copolymers of this family include the product Salcare $SC_{92}$ sold by Ciba-Allied Colloids and the product PAS 5194 sold by Hoechst. These polymers and preparations thereof are described in document EP 395 282.

The composition may also comprise nonionic guar gums, for example, the unmodified nonionic guar gums sold under the name Vidogum GH 175 by the company Unipectine and under the name Jaguar C by the company Meyhall.

The nonionic guar gums that may be used may be optionally modified with $C_1$-$C_6$ hydroxyalkyl groups, for example, hydroxymethyl, hydroxyethyl, hydroxypropyl and hydroxybutyl groups.

Guar gums are well known in the prior art and can be prepared, for example, by reacting the corresponding alkene oxides such as, for example, propylene oxides, with the guar gum to obtain a guar gum modified with hydroxypropyl groups.

The degree of hydroxyalkylation, which corresponds to the number of alkylene oxide molecules consumed by the number of free hydroxyl functions present on the guar gum, may range from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall or under the name Galactasol 4H4FD2 by the company Aqualon.

Examples of suitable non-associative thickening polymers include biopolysaccharide gums of microbial origin, such as scleroglucan gum or xanthan gum.

Gums derived from plant exudates, such as gum arabic, ghatti gum, karaya gum and gum tragacanth; hydroxypropyl- or carboxymethyl celluloses; pectins and alginates, may also be used.

These polymers are known to those skilled in the art and are described in Robert L. Davidson, "Handbook of Water soluble gums and resins," McGraw-Hill Book Company (1980).

Thickening systems based on associative polymers that are known to those skilled in the art may be used, for example, nonionic, anionic, cationic or amphoteric thickeners.

Associative polymers are hydrophilic polymers capable, in an aqueous medium, of reversibly associating with each other or with other molecules. Their chemical structure comprises at least one hydrophilic region and at least one hydrophobic region. As used herein, the term "hydrophobic group" means a radical or polymer containing a saturated or unsaturated, linear or branched, hydrocarbon-based chain having at least ten carbon atoms, for example, from 10 to 30, 12 to 30, or 18 to 30 carbon atoms. Optionally, the hydrocarbon-based group originates from a monofunctional compound. For example, the hydrophobic group may be derived from a fatty alcohol such as stearyl alcohol, dodecyl alcohol or decyl alcohol. It may also be a hydrocarbon-based polymer, for example, polybutadiene.

The composition may thus comprise at least one associative polymer chosen from associative polyurethanes, which may be cationic or nonionic, associative cellulose derivatives, for example, cationic or nonionic, associative vinyllactams, associative unsaturated polyacids, associative aminoplastethers, associative polymers or copolymers comprising at least one ethylenically unsaturated monomer containing a sulfonic group, alone or as mixtures.

Associative thickening polymers include, for example, associative polyurethane derivatives, such as those obtained by polymerization of:

about 20% to 70% by weight of an $\alpha,\beta$-monoethylenically unsaturated carboxylic acid, about 20% to 80% by weight of a non-surfactant $\alpha,\beta$-monoethylenically unsaturated monomer, different from the previous monomer, and about 0.5% to 60% by weight of a nonionic monourethane, which is the product of reaction of a monohydroxylated surfactant with a monoethylenically unsaturated monoisocyanate.

Such polymers are described in EP 173 109 (Example 3), i.e., a methacrylic acid/methyl acrylate/dimethyl meta-isopropenyl benzyl isocyanate terpolymer of ethoxylated behenyl alcohol (40 EO) as an aqueous 25% dispersion and sold under the name Viscophobe DB1000 by the company Amerchol.

The family of cationic associative polyurethanes may be used, and has been described in patent application FR 0 009 609, i.e., polyurethanes of the general formula (A):

$$R-X-(P)_n-[L-(Y)_m]_r-L'-(P')_p-X'-R' \quad (A)$$

wherein:

R and R', which may be identical or different, each are a hydrophobic group or a hydrogen atom;

X and X', which may be identical or different, each are a group comprising an amine function optionally bearing a hydrophobic group, or alternatively a group L";

L, L' and L," which may be identical or different, each are a group derived from a diisocyanate;

P and P', which may be identical or different, each are a group comprising an amine function optionally bearing a hydrophobic group;

Y is a hydrophilic group;

r is an integer ranging from 1 to 100, for example, 1 to 50 or 1 to 25; and n, m and p each range, independently of each other, from 0 to 1000; the molecule containing at least one protonated or quaternized amine function and at least one hydrophobic group.

In one embodiment, the only hydrophobic groups are the groups R and R' at the chain ends.

In some embodiments, the associative polyurethane corresponds to formula (A) wherein R and R' each independently is a hydrophobic group; X and X' each represent a group L"; n and p each range from 1 to 1000, and L, L', L," P, P', Y and m are as descried above in formula (A).

In some embodiments, the associative polyurethane corresponds to formula (A) in which R and R' each independently is a hydrophobic group, X and X' each independently is a group L", n and p are each 0, and L, L', L," Y and m have the meaning as in formula (A) above.

The fact that n and p are 0 means that these polymers do not comprise units derived from a monomer comprising an amine function, incorporated into the polymer during the polycondensation. The protonated amine functions of these polyurethanes result from the hydrolysis of excess isocyanate functions, at the chain end, followed by alkylation of the primary amine functions formed with alkylating agents comprising a hydrophobic group, e.g., compounds of the type RQ or R'Q, wherein R and R' are as defined above and Q denotes a leaving group such as a halide, a sulfate, etc.

In other embodiments, the associative polyurethane corresponds to formula (A) wherein R and R' each independently represent a hydrophobic group; X and X' each independently represent a group comprising a quaternary amine; n and p are each zero and L, L', Y and m have the meaning indicated in formula (A).

The number-average molecular mass of the cationic associative polyurethanes may range from 400 to 500,000, for example, from 1000 to 400,000 g/mol or 1000 to 300,000 g/mol.

When X and/or X' denote a group comprising a tertiary or quaternary amine, X and/or X' may be chosen from the following formulae:

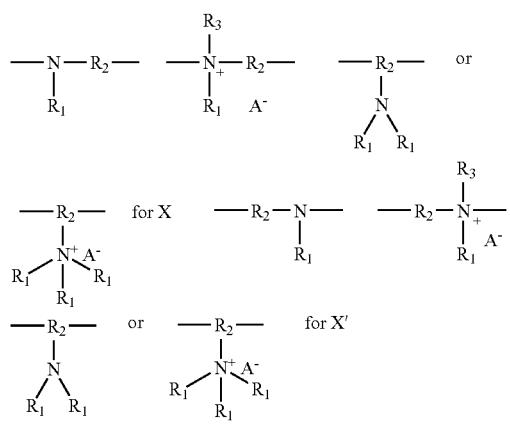

wherein:
R₂ is a linear or branched alkylene radical having from 1 to 20 carbon atoms, optionally comprising a saturated or unsaturated ring, or an arylene radical, one or more of the carbon atoms optionally being replaced with a heteroatom chosen from N, S, O and P;
R₁ and R₃, which may be identical or different, are chosen from linear and branched $C_1$-$C_{30}$ alkyl or alkenyl radicals and aryl radicals, at least one of the carbon atoms optionally being with a heteroatom chosen from N, S, O and P; and
A⁻ is a physiologically acceptable counterion.

The groups L, L' and L" are each chosen from a group of the formula:

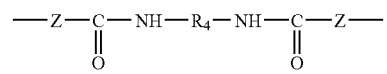

wherein:
Z is chosen from —O—, —S—, and —NH—; and
R₄ is chosen from linear and branched alkylene radicals having from 1 to 20 carbon atoms optionally comprising a saturated or unsaturated ring, and arylene radicals, one or more of the carbon atoms possibly being replaced with a heteroatom chosen from N, S, O and P.

The groups P and P' comprising an amine function may represent at least one of the following formulae:

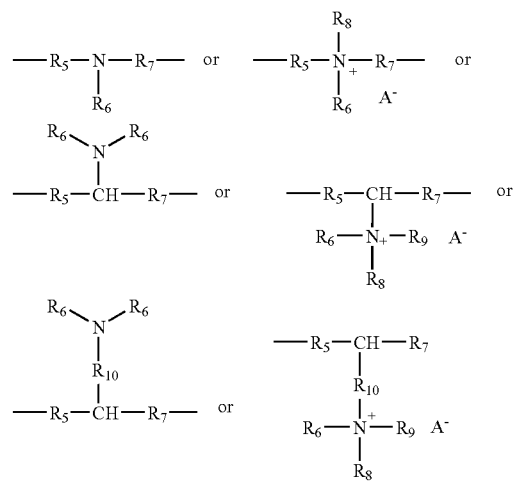

wherein:
R₅ and R₇ have the meanings as R₂ defined above;
R₆, R₈ and R₉ have the meanings as R₁ and R₃ defined above;
R₁₀ is chosen from linear or branched, optionally unsaturated alkylene groups optionally comprising one or more heteroatoms chosen from N, O, S and P; and
A⁻ is a cosmetically acceptable counterion.

With respect to the meaning of Y, the term "hydrophilic group" means a polymeric or non-polymeric water-soluble group. When Y is not a polymer, it may be, for example, ethylene glycol, diethylene glycol, or propylene glycol. In some embodiments, it is a hydrophilic polymer chosen from, for example, polyethers, sulfonated polyesters, sulfonated polyamides, and mixtures of these polymers. The hydrophilic compound may be a polyether such as poly(ethylene oxide) or poly(propylene oxide).

The associative polyurethanes of formula (A) are formed from diisocyanates and from various compounds with functions comprising a labile hydrogen. The functions comprising a labile hydrogen may be, for example, alcohol, primary or secondary amine or thiol functions, giving, after reaction with the diisocyanate functions, polyurethanes, polyureas and polythioureas, respectively. As used herein, the term "polyurethanes" encompasses these three types of polymers, i.e., polyurethanes per se, polyureas and polythioureas, as well as copolymers thereof.

A first type of compound included in the preparation of the polyurethane of formula (A) is a compound comprising at least one unit containing an amine function. This compound may be multifunctional, e.g., difunctional, i.e., comprising two labile hydrogen atoms borne, for example, by a hydroxyl, primary amine, secondary amine or thiol function.

A mixture of multifunctional and difunctional compounds in which the percentage of multifunctional compounds is low may also be used.

As mentioned above, the compound may comprise more than one unit containing an amine function, i.e., it may be a polymer bearing a repetition of the unit containing an amine function.

Compounds of this type may be represented by the following formula:

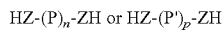

HZ-(P)$_n$-ZH or HZ-(P')$_p$-ZH wherein Z, P, P', n and p are as defined above.

Examples of compounds containing an amine function include, but are not limited to, N-methyldiethanolamine, N-tert-butyldiethanolamine, and N-sulfoethyldiethanolamine.

The second compound included in the preparation of the polyurethane of formula (A) is a diisocyanate corresponding to the formula O=C=N—R$_4$—N=C=O, wherein R$_4$ is as defined above.

Examples include methylenediphenyl diisocyanate, methylenecyclohexane diisocyanate, isophorone diisocyanate, toluene diisocyanate, naphthalene diisocyanate, butane diisocyanate, and hexane diisocyanate.

A third compound included in the preparation of the polyurethane of formula (A) is a hydrophobic compound intended to form the terminal hydrophobic groups of the polymer of formula (A).

This compound comprises a hydrophobic group and a function containing a labile hydrogen, for example a hydroxyl, primary or secondary amine, or thiol function.

For example, this compound may be a fatty alcohol such as stearyl alcohol, dodecyl alcohol or decyl alcohol. When this compound comprises a polymeric chain, it may be, for example, α-hydroxylated hydrogenated polybutadiene.

The hydrophobic group of the polyurethane of formula (A) may also result from a quaternization reaction of the tertiary amine of the compound comprising at least one tertiary amine unit. Thus, the hydrophobic group is introduced via the quaternizing agent. This quaternizing agent is a compound of the formula RQ or R'Q, in which R and R' are as defined above and Q is a leaving group such as a halide, a sulfate, etc.

The cationic associative polyurethane may also comprise a hydrophilic block. This block is provided by a fourth type of compound involved in the preparation of the polymer, which may be multifunctional such as difunctional. It is possible to have a mixture in which the percentage of multifunctional compound is low.

The functions containing a labile hydrogen are, for example, alcohol, primary or secondary amine and thiol functions. This compound may be a polymer terminated at the chain ends with one of these functions containing a labile hydrogen.

For example, when it is not a polymer it may be made of ethylene glycol, diethylene glycol or propylene glycol.

When it is a hydrophilic polymer, it may be, for example, polyethers, sulfonated polyesters and sulfonated polyamides, or a mixture of these polymers.

The hydrophilic compound may be a polyether, for example, a poly(ethylene oxide) or poly(propylene oxide).

The hydrophilic group termed Y in formula (A) is optional. The units containing a quaternary amine or protonated function may suffice to provide the solubility or water-dispersibility required for this type of polymer in an aqueous solution.

Although the presence of a hydrophilic group Y is optional, cationic associative polyurethanes comprising such a group may be used.

The associative polyurethane derivatives may also be nonionic polyurethane polyethers. The polymers may comprise in their chain both polyoxyethylenated hydrophilic blocks and hydrophobic blocks that may be aliphatic chains alone and/or cycloaliphatic and/or aromatic chains.

The polyurethane polyethers may comprise at least two hydrocarbon-based lipophilic chains, having from 6 to 30 carbon atoms, separated by a hydrophilic block, the hydrocarbon-based chains optionally being pendent chains or chains at the end of a hydrophilic block. For example, it is possible for one or more pendent chains to be provided. In addition, the polymer may comprise a hydrocarbon-based chain at one or both ends of a hydrophilic block.

The polyurethane polyethers may be multiblock, e.g., in triblock form. The hydrophobic blocks may be at each end of the chain (for example: triblock copolymer containing a hydrophilic central block) or distributed both at the ends and in the chain (for example: multiblock copolymer). These polymers may also be graft polymers or starburst polymers.

The fatty-chain nonionic polyurethane polyethers may be triblock copolymers whose hydrophilic block is a polyoxyethylenated chain comprising from 50 to 1000 oxyethylenated groups.

The nonionic polyurethane polyethers comprise a urethane bond between the hydrophilic blocks, whence arises the name.

By extension, hydrophobic-chain nonionic polyurethane polyethers also include those having hydrophilic blocks that are linked to the hydrophobic blocks via other chemical bonds.

Examples of hydrophobic-chain nonionic polyurethane polyethers that may be used include Rheolate 205® containing a urea function, sold by the company Rheox and Rheolates® 208, 204 or 212 or Acrysol RM 184®.

The product Elfacos T210® containing a C$_{12-14}$ alkyl chain and the product Elfacos T212® containing a C$_{18}$ alkyl chain, from Akzo, may also be used.

The product DW 1206B® from Rohm & Haas containing a C$_{20}$ alkyl chain and a urethane linkage, sold at a solids content of 20% in water, may also be used.

It is also possible to use solutions or dispersions of these polymers, for example, in water or in aqueous-alcoholic media. Examples of such polymers include Rheolate® 255, Rheolate® 278 and Rheolate® 244 sold by the company Rheox. The products DW 1206F and DW 1206J sold by the company Rohm & Haas may also be used.

The polyurethane polyethers that may be used, may also be chosen from those described in the article G. Formum, J. Bakke and F k. Hansen—Colloid Polym. Sci. 271, 380-389 (1993).

In some embodiments, a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate, is used.

Such polyurethane polyethers are sold, for example, by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%)].

The composition may also comprise polymers derived from associative celluloses, such as:
- quaternized cationic celluloses modified with groups comprising at least one hydrophobic chain, such as alkyl, arylalkyl or alkylaryl groups containing at least 8 carbon atoms, and mixtures thereof, and
- quaternized cationic hydroxyethylcelluloses modified with groups comprising at least one hydrophobic chain, such as alkyl, arylalkyl or alkylaryl groups containing at least 8 carbon atoms, and mixtures thereof.

The alkyl radicals borne by the above quaternized celluloses or hydroxyethylcelluloses may have from 8 to 30 carbon atoms. The aryl radicals may be, for example, phenyl, benzyl, naphthyl or anthryl groups.

Examples of quaternized alkylhydroxyethylcelluloses containing $C_8$-$C_{30}$ hydrophobic chains that may be used include:
- the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.
- nonionic cellulose derivatives such as hydroxyethyl celluloses modified with groups comprising at least one hydrophobic chain, such as alkyl, arylalkyl or alkylaryl groups, or mixtures thereof, and in which the alkyl groups may be $C_8$-$C_{22}$ groups, for example, the product Natrosol Plus Grade 330 CS® ($C_{16}$ alkyls) sold by the company Aqualon, or the product Bermocoll EHM 100® sold by the company Berol Nobel, and
- cellulose derivatives modified with polyalkylene glycol alkylphenol ether groups, such as the product Amercell Polymer HM-1500® sold by the company Amerchol.

Examples of associative polyvinyllactams that may be used include the polymers described in FR 0 101 106. These polymers are cationic polymers and comprise:
(1) at least one vinyllactam or alkylvinyllactam monomer;
(2) at least one monomer of structure (a) or (b) below:

wherein:
X is chosen from an oxygen atom or a $NR_6$ radical,
$R_1$ and $R_6$ are chosen from, independently of each other, a hydrogen atom and linear or branched $C_1$-$C_5$ alkyl radicals,
$R_2$ is a linear or branched $C_1$-$C_4$ alkyl radical,
$R_3$, $R_4$ and $R_5$ are chosen from, independently of each other, a hydrogen atom, linear and branched $C_1$-$C_{30}$ alkyl radicals, and radicals of formula (c):

$$-(Y_2)_r-(CH_2-CH(R_7)-O)_x-R_8 \quad (c)$$

Y, $Y_1$ and $Y_2$ are chosen from, independently of each other, linear and branched $C_2$-$C_{16}$ alkylene radicals,
$R_7$ is chosen from a hydrogen atom, linear and branched $C_1$-$C_4$ alkyl radicals, and linear or branched $C_1$-$C_4$ hydroxyalkyl radicals,
$R_8$ is chosen from a hydrogen atom and linear and branched $C_1$-$C_{30}$ alkyl radicals,
p, q and r are, independently of each other, either the value 0 or the value 1,
m and n are, independently of each other, an integer ranging from 0 to 100,
x is an integer ranging from 1 to 100, and
$Z^-$ is an organic or mineral acid anion, with the proviso that:
at least one of the substituents $R_3$, $R_4$, $R_5$ or $R_8$ is a linear or branched $C_9$-$C_{30}$ alkyl radical,
if m or n is other than zero, then q is equal to 1,
if m or n is equal to zero, then p or q is equal to 0.

The poly(vinyllactam) polymers may be crosslinked or non-crosslinked and may also be block polymers.

The counterion $Z^-$ of the monomers of formula (b) is chosen from halide ions, phosphate ions, the methosulfate ion, and the tosylate ion.

In some embodiments, $R_3$, $R_4$ and $R_5$ are, independently of each other, a hydrogen atom or a linear or branched $C_1$-$C_{30}$ alkyl radical.

In some embodiments, the monomer (2) is a monomer of formula (b). In certain of these embodiments, m and n are equal to zero.

The vinyllactam or alkylvinyllactam monomer may be a compound of formula (d):

$$CH(R_9)=C(R_{10})-N\underset{(CH_2)_s}{\overset{\diagup}{\diagdown}}=O \quad (d)$$

wherein:
s is an integer ranging from 3 to 6,
$R_g$ is a hydrogen atom or a $C_1$-$C_5$ alkyl radical, and
$R_{10}$ is a hydrogen atom or a $C_1$-$C_5$ alkyl radical, $$CH_2=C(R_1)-CO-X-(Y)_p-(CH_2-CH_2-O)_m-(CH_2-CH(R_2)-O)_n-(Y_1)_q-\overset{R_3}{\underset{R_5}{\overset{|}{N^+}}}-R_4 \quad Z^- \quad (a)$$

$$CH_2=C(R_1)-CO-X-(Y)_p-(CH_2-CH_2-O)_m-(CH_2-CH(R_2)-O)_n-(Y_1)_q-N\underset{R_4}{\overset{R_3}{\diagup\diagdown}} \quad (b)$$

with the proviso that at least one of the radicals $R_9$ and $R_{10}$ is a hydrogen atom.

In some embodiments, the monomer (d) is vinylpyrrolidone.

The poly(vinyllactam) polymers may also comprise one or more additional monomers, such as cationic or nonionic monomers.

In some embodiments, the following terpolymers are used, which comprise at least:
(1) one monomer of formula (d),
(2) one monomer of formula (a) in which p=1, q=0, $R_3$ and $R_4$ are, independently of each other, a hydrogen atom or a $C_1$-$C_5$ alkyl radical and $R_5$ is a $C_9$-$C_{24}$ alkyl radical, and
(3) a monomer of formula (b) in which $R_3$ and $R_4$ are, independently of each other, a hydrogen atom or a $C_1$-$C_5$ alkyl radical.

In some embodiments, terpolymers comprising, by weight, from 40% to 95% of monomer (d), from 0.1% to 55% of monomer (a) and from 0.25% to 50% of monomer (b) are used.

Such polymers are described in WO 00/68282, which is hereby incorporated by reference.

Poly(vinyllactam) polymers, vinylpyrrolidone/dimethylaminopropylmethacrylamide/dodecyldimethylmethacrylamidopropylammonium, tosylate terpolymers, vinylpyrrolidone/dimethylaminopropylmethacrylamide/cocoyldimethylmethacrylamidopropylammonium, tosylate terpolymers, vinylpyrrolidone/dimethylaminopropylmethacrylamide/lauryldimethylmethacrylamidopropylammonium, tosylate or chloride terpolymers may be used. The vinylpyrrolidone/dimethylaminopropylmethacrylamide/lauryldimethylmethacrylamidopropylammonium, chloride terpolymer is sold at a concentration of 20% in water by the company ISP under the name Styleze W20.

The associative polyvinyllactam derivatives may also be nonionic copolymers of vinylpyrrolidone and of hydrophobic monomers comprising a hydrophobic chain, for example the products Antaron V216® or Ganex V216® (vinylpyrrolidone/hexadecene copolymer) sold by the company ISP, and the products Antaron V220® or Ganex V220® (vinylpyrrolidone/eicosene copolymer) sold by the company ISP.

Associative unsaturated polyacid derivatives that may be used include those comprising at least one unsaturated olefinic carboxylic acid hydrophilic unit, and at least one unsaturated carboxylic acid ($C_{10}$-$C_{30}$) alkyl ester hydrophobic unit.

These polymers may be chosen from those in which the unsaturated olefinic carboxylic acid hydrophilic unit corresponds to the monomer of formula (e) below:

wherein $R_1$ is H, $CH_3$ or $C_2H_5$, i.e., acrylic acid, methacrylic acid or ethacrylic acid units, and in which the ($C_{10}$-$C_{30}$) alkyl ester of an unsaturated carboxylic acid hydrophobic unit corresponds to the monomer of formula (f) below:

wherein $R_2$ is H or $CH_3$ or $C_2H_5$, i.e. acrylate, methacrylate or ethacrylate units, for example, H (acrylate units) or $CH_3$ (methacrylate units), $R_3$ is a $C_{10}$-$C_{30}$ or even $C_{12}$-$C_{22}$ alkyl radical. ($C_{10}$-$C_{30}$)Alkyl esters of unsaturated carboxylic acids may comprise, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate, and dodecyl methacrylate.

Such anionic polymers are disclosed and prepared, for example, according to U.S. Pat. Nos. 3,915,921 and 4,509,949.

Polymers formed from a mixture of monomers comprising:
(i) acrylic acid,
(ii) an ester of formula (f) described above, wherein $R_2$ is H or $CH_3$, $R_3$ is an alkyl radical having from 12 to 22 carbon atoms, and
(iii) a crosslinking agent, for example, a well-known copolymerizable polyethylenic unsaturated monomer, e.g., diallyl phthalate, allyl (meth)acrylate, divinylbenzene, (poly)ethylene glycol dimethacrylate, and methylenebisacrylamide may be used.

The anionic associative polymers that may be used include those having from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those having from 96% to 98% by weight of acrylic acid (hydrophilic unit), 1% to 4% by weight of $C_{10}$-$C_{30}$ alkyl acrylate (hydrophobic unit), and 0.1% to 0.6% by weight of a crosslinking polymerizable monomer such as those described above.

Among the polymers described above, the products sold by the company Goodrich under the trade names Pemulen $TR_1$®, Pemulen $TR_2$®, Carbopol 1382®, Pemulen $TR_1$®, and the product sold by the company SEPPIC under the name Coatex SX® may be used.

Associative unsaturated polyacid derivatives that may used include those comprising α,β-monoethylenically unsaturated carboxylic acid and an ester of an α,β-monoethylenically unsaturated carboxylic acid and of an oxyalkylenated fatty alcohol monomers.

These compounds may also comprise as a monomer an ester of an α,β-monoethylenically unsaturated carboxylic acid and of a $C_1$-$C_4$ alcohol.

Aculyn 22® sold by the company Rohm & Haasis a methacrylic acid/ethyl acrylate/oxyalkylenated stearyl methacrylate terpolymer that may be used.

Aminoplast-ether thickening polymers include any product derived from the condensation of an aldehyde with an amine or an amide, and any structural unit formed from an aminoplast residue and from a divalent hydrocarbon-based residue linked to the aminoplast residue via an ether bond, is designated.

The polymers with an aminoplast-ether skeleton may be chosen from those comprising at least one unit of structure (g) below:

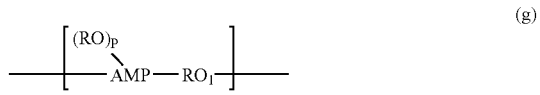

wherein:
AMP is an aminoplast residue with alkylene units (or divalent alkyl),
R is chosen from a hydrogen atom, a $C_1$-$C_4$ alkyl radicals, and $C_1$-$C_4$ acyl radicals,
$RO_1$ is a divalent alkyleneoxy residue, and p is a positive integer, the group(s) OR being linked to the alkylene units of the AMP residue.

The polymers with an aminoplast-ether skeleton may be chosen from those comprising at least one unit of structure (h) below:

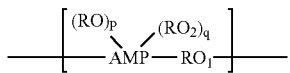
(h)

wherein:
AMP, R, $RO_1$ and p have the same meaning as above,
$RO_2$ is a group other than RO linked to AMP via a heteroatom and comprising at least two carbon atoms, and
q is a positive integer.

In some embodiments, the polymers correspond to formulae (III) and (IIIa) below:

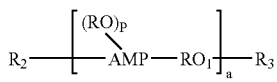
(iii)

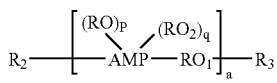
(iiia)

wherein:
AMP, R, $RO_1$, $RO_2$, p and q have the same meaning as above,
$R_2$ or $R_3$, which may be identical or different, are each an end group chosen from a hydrogen atom, a group $RO_1H$, a group $RO_2H$, a group $AMP(OR)p$ or any monofunctional group such as alkyl, cycloalkyl, aryl, aralkyl, alkylaryl, alkyloxyalkyl, aryloxyalkyl or cycloalkoxyalkyl, and
a is a number greater than 1, for example, greater than 2.

The aminoplast residues bearing the groups OR thereof integrated into the polymers may be chosen from, for example, structures (1) to (12) below:

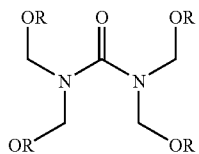
(1)

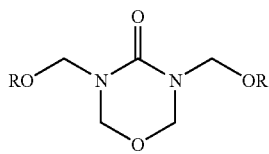
(2)

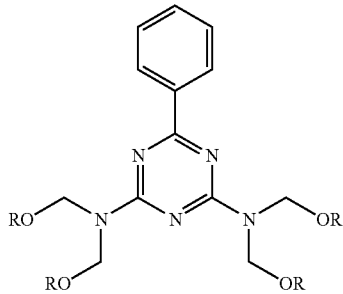
(3)

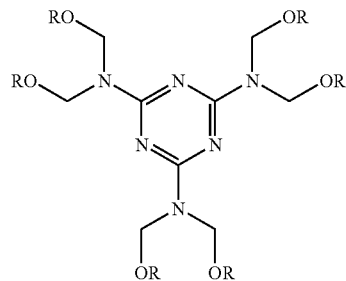
(4)

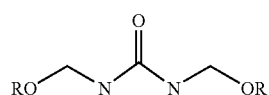
(5)

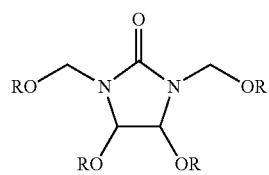
(6)

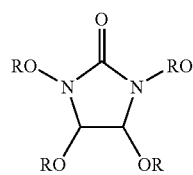
(7)

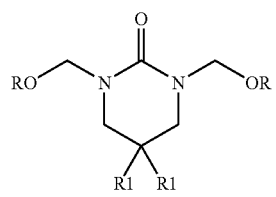
(8)

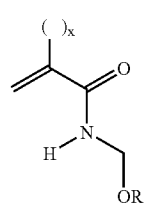
(9)

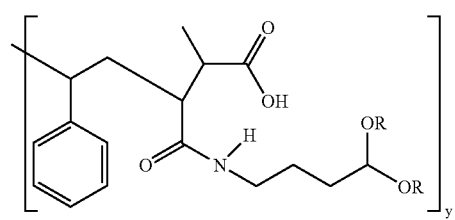
(10)

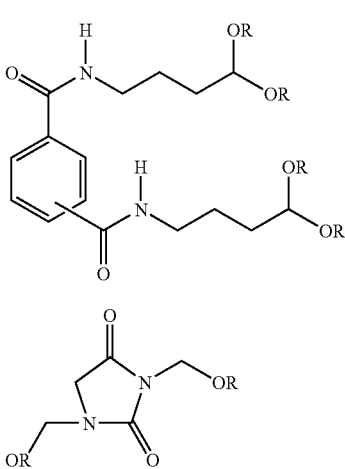

wherein:
R has the same meaning as above,
$R_1$ is $C_1$-$C_4$ alkyl,
y is greater than or equal to 2, and
x is 0 or 1.

The aminoplast residues bearing the groups OR may be chosen groups of structure (13):

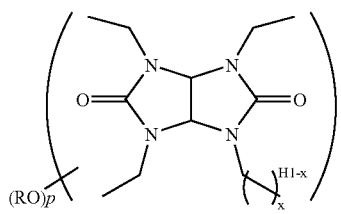

wherein R, p and X have the same meanings as above.

The divalent alkyleneoxy residues may be chosen from those corresponding to the diols of general formula (14):

$$HO\text{-}(ZO)_y\text{-}(Z_1(Z_2O)_w)_t\text{-}(Z'O)_{y'}\text{-}Z_3OH \qquad (14)$$

wherein:
y and y' are each independently numbers ranging from 0 to 1000,
t and w are each independently numbers ranging from 0 to 10,
Z, Z', $Z_2$ and $Z_3$ are each independently chosen from $C_2$-$C_4$ alkylene radicals, for example, the radicals —$CH_2$—CH($Z_4$)— and —$CH_2$—CH($Z_4$)—$CH_2$—,
$Z_1$ is chosen from linear and cyclic, branched and unbranched, aromatic and non-aromatic radicals optionally comprising one or more heteroatoms and having from 1 to 40 carbon atoms, and
$Z_4$ is chosen from a hydrogen atom, $C_1$-$C_4$ alkyl radicals, and $C_1$-$C_3$ acyl radicals, wherein at least one of the radicals $Z_4$ of the radicals Z, Z', $Z_2$ and $Z_3$ is other than an acyl radical.

In some embodiments, $Z_4$ denotes a hydrogen atom or a methyl radical.

In some embodiments, t=0 and Z, Z' and $Z_3$ are each —$CH_2CH_2$—, and at least one y and y' is other than 0. The compounds of formula (14) are then polyethylene glycols.

The aminoplast-ether polymers of formula (g) are described in U.S. Pat. No. 5,914,373, which discloses further details.

Polymers with an aminoplast-ether skeleton of formula (g) include the products Pure-Thix® L [PEG-180/Octoxynol-40/TMMG Copolymer (INCI name)], Pure-Thix M® [PEG-180/Laureth-50/TMMG Copolymer (INCI name)], and Pure-Thix® HH [Polyether-1 (INCI name)]; Pure-Thix TX-1442® [PEG-18/dodoxynol-5/PEG-25 tristyrylphenol/tetramethoxy methyl glycoluril copolymer], sold by the company Süd-Chemie.

The thickening polymers may also be chosen from associative polymers comprising at least one ethylenically unsaturated monomer having a sulfonic group, in free or partially or totally neutralized form, and comprising at least one hydrophobic portion.

These polymers may be partially or totally neutralized with a mineral base (sodium hydroxide, potassium hydroxide or aqueous ammonia) or an organic base such as monoethanolamine, diethanolamine, triethanolamine, an aminomethylpropanediol, N-methylglucamine, basic amino acids, for instance arginine and lysine, and mixtures of these compounds.

These associative polymers may or may not be crosslinked; in some embodiments, they are crosslinked polymers. In certain embodiments, the cross-linking agents are derived from at least one monomer comprising at least two ethylenic unsaturations (carbon-carbon double bonds).

The crosslinking monomers comprising at least two ethylenic unsaturations may be chosen from, for example, diallyl ether, triallyl cyanurate, diallyl maleate, allyl (meth)acrylate, dipropylene glycol diallyl ether, polyglycol diallyl ethers, triethylene glycol divinyl ether, hydroquinone diallyl ether, tetraallyloxethanoyl, ethylene glycol di(meth)acrylate or tetraethylene glycol di(meth)acrylate, triallylamine, tetraallylethylenediamine, trimethylolpropane diallyl ether, trimethylolpropane triacrylate, methylenebis(meth)acrylamide or divinylbenzene, allylic ethers of alcohols of the sugars, other allyl or vinyl ethers of polyfunctional alcohols, allylic esters of phosphoric and/or vinylphosphonic acid derivatives, and mixtures of these compounds.

In some embodiments, methylenebisacrylamide, allyl methacrylate or trimethylolpropane triacrylate are used. The degree of crosslinking may range from 0.01 mol % to 10 mol % relative to the polymer.

The ethylenically unsaturated monomers comprising a sulfonic group may be chosen from vinylsulfonic acid, styrenesulfonic acid, (meth)acrylamido($C_1$-$C_{22}$)alkylsulfonic acids, and N-($C_1$-$C_{22}$)alkyl(meth)acrylamido($C_1$-$C_{22}$)alkylsulfonic acids, for example, undecylacrylamidomethanesulfonic acid, and also partially or totally neutralized forms thereof.

(Meth)acrylamido($C_1$-$C_{22}$)alkylsulfonic acids such as, for example, acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4trimethylpentanesulfonic acid, 2-methacrylamidododecylsulfonic acid, 2-acrylamido-2,6-dimethyl-3-heptanesulfonic acid, and also partially or totally neutralized forms thereof, may be used.

In some embodiments, 2-acrylamido-2-methylpropanesulfonic acid (AMPS), and also partially or totally neutralized forms thereof, are used.

The amphiphilic polymers present in the compositions may also be chosen from random amphiphilic AMPS polymers modified by reaction with a $C_6$-$C_{22}$ n-monoalkylamine or di-n-alkylamine, and such as those described in patent application WO 00/31154.

The hydrophobic monomers that constitute the hydrophobic portion of the polymer may be chosen from acrylates or acrylamides of formula (k):

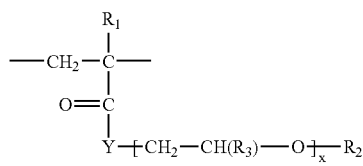

wherein:
- $R_1$ and $R_3$, which may be identical or different, are each chosen from a hydrogen atom and linear and branched $C_1$-$C_6$ alkyl radicals (such as methyl);
- Y is O or NH;
- $R_2$ is a hydrophobic hydrocarbon-based radical as defined previously; and
- x is a number of moles of alkylene oxide and ranges from 0 to 100.

The radical $R_2$ may be chosen from linear $C_6$-$C_{18}$ alkyl radicals (for example n-hexyl, n-octyl, n-decyl, n-hexadecyl and n-dodecyl) and branched or cyclic $C_6$-$C_{18}$ alkyl radicals (for example cyclododecane ($C_{12}$) or adamantane ($C_{10}$)); $C_6$-$C_{18}$ alkylperfluoro radicals (for example the group of formula —$(CH_2)_2$—$(CF_2)_9$—$CF_3$); the cholesteryl radical ($C_{27}$) or a cholesterol ester residue, for example, the cholesteryl oxyhexanoate group; aromatic polycyclic groups, for example, naphthalene or pyrene. In some embodiments, linear alkyl radicals are used, such as an n-dodecyl radical.

In some embodiments, the monomer of formula (k) comprises at least one alkylene oxide unit ($x \geq 1$) and optionally a polyoxyalkylenated chain. The polyoxyalkylenated chain may comprise ethylene oxide units and/or propylene oxide units, for example, ethylene oxide units. The number of oxyalkylene units generally ranges from 3 to 100, such as from 3 to 50 or from 7 to 25.

The copolymers may also comprise other ethylenically unsaturated hydrophilic monomers, chosen, for example, from (meth)acrylic acids, β-substituted alkyl derivatives thereof and esters thereof obtained with monoalcohols or mono- or polyalkylene glycols, (meth)acrylamides, vinylpyrrolidone, maleic anhydride, itaconic acid, maleic acid, and mixtures of these compounds.

These copolymers are described in, for example, documents EP 750 899 and U.S. Pat. No. 5,089,578 and in the following publications from Yotaro Morishima: "Self-assembling amphiphilic polyelectrolytes and their nanostructures—Chinese Journal of Polymer Science Vol. 18, No. 40, (2000), 323-336"; "Micelle formation of random copolymers of sodium, 2-(acrylamido)-2-methylpropanesulfonate and a nonionic surfactant macromonomer in water as studied by fluorescence and dynamic light scattering—Macromolecules 2000, Vol. 33, No. 10-3694-3704"; "Solution properties of micelle networks formed by nonionic moieties covalently bound to a polyelectrolyte: salt effects on Theological behaviour—Langmuir, 2000, Vol. 16, No. 12, 5324-5332"; "Stimuli responsive amphiphilic copolymers of sodium, 2-(acrylamido)-2-methylpropanesulfonate and associative macromonomers—Polym. Preprint, Div. Polym. Chem. 1999, 40(2), 220-221".

The distribution of the monomers in the copolymer may be in random or block form.

Polymers of this type, include, but are not limited to:
- crosslinked or non-crosslinked, neutralized or non-neutralized copolymers comprising from 15% to 60% by weight of AMPS units and from 40% to 85% by weight of ($C_8$-$C_{16}$)alkyl(meth)acrylamide units or of ($C_8$-$C_{16}$) alkyl (meth)acrylate units, relative to the polymer, such as those described in patent application EP-A-750 899;
- terpolymers comprising from 10 mol % to 90 mol % of acrylamide units, from 0.1 mol % to 10 mol % of AMPS units and from 5 mol % to 80 mol % of n-($C_6$-$C_{18}$) alkylacrylamide units, such as those described in U.S. Pat. No. 5,089,578;
- copolymers of totally neutralized AMPS and of dodecyl methacrylate, and also crosslinked and non-crosslinked copolymers of AMPS and of n-dodecylmethacrylamide, such as those described in the Morishima articles listed above.

It is also possible to use copolymers comprising AMPS units of formula (I)

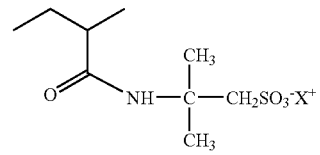

wherein $X^+$ is as described above, and of units of formula (I) below:

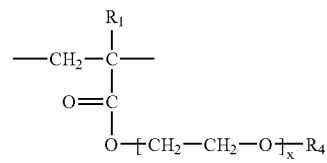

wherein x is an integer ranging from 3 to 100, for example, from 5 to 80 or even from 7 to 25; $R_1$ has the same meaning as above in formula (I) and $R_4$ is a linear or branched $C_6$-$C_{22}$ alkyl, for example, $C_{10}$-$C_{22}$ alkyl.

In some embodiments, x=25, $R_1$ is methyl and $R_4$ is n-dodecyl, described in the Morishima articles above.

In some embodiments, polymers in which $X^+$ is sodium or ammoniumare used.

Genapol® polymers from the company Hoechst/Clariant may be used.

The concentration of associative or non-associative thickening polymers present in the compositions may range from 0.01% to 10% by weight, for example, from 0.1% to 5% or even from 0.5% to 5% by weight, relative to the weight of the composition.

Needless to say, a person skilled in the art will take care to select this or these optional additional compounds such that the beneficial properties intrinsically associated with the compositions are not, or are not substantially, adversely affected by the envisaged additions.

The compositions may be in various forms, such as in the form of liquids, shampoos, creams or gels, or in any other suitable form.

In some embodiments, the compositions are in the form or a dyeing and/or lightening shampoo comprising, in a cosmetically acceptable aqueous medium, at least one direct dye as defined above, and at least one surfactant, which may be nonionic.

In some embodiments, the nonionic surfactants are alkylpolyglucosides.

In some embodiments, the compositions further comprise at least one oxidizing agent chosen, for example, from hydrogen peroxide, urea peroxide, alkali metal bromates, persalts such as perborates and persulfates, and enzymes such as peroxidases and two-electron or four-electron oxidoreductases. In certain embodiments, hydrogen peroxide or enzymes are used.

The disclosure also provides processes for treating keratin fibers including human keratin fibers.

According to a first embodiment of the process, a composition as defined herein is applied to the fibers, which may be wet or dry fibers, for a sufficient time, after which the fibers are rinsed, optionally washed with shampoo, rinsed again and dried, or the resulting fibers are left to dry.

According to a second embodiment of the process, a composition as defined is applied to the said wet or dry fibers without final rinsing.

The first embodiment may be used for compositions of any type, whether or not they comprise an oxidizing agent and/or a direct dye and/or an oxidation base optionally combined with a coupler.

The second embodiment is suitable for compositions not comprising an oxidation dye (oxidation base and optionally coupler) or an oxidizing agent.

In the case of the first embodiment, the application time is usually sufficient to develop the desired coloration and/or lightening.

As a guide, the application time for the composition may range from about 5 to 60 minutes such as from about 15 to 60 minutes.

Moreover, the temperature at which the processes is performed is generally from room temperature (25° C.) to 60° C. or even from 15 to 45° C. or 15 to 60° C.

When the compositions comprise an oxidizing agent, the processes comprise a preliminary step that comprises separately storing, first, a composition comprising, in a cosmetically acceptable medium, at least one direct dye of formula (I) or (I'), optionally at least one additional direct dye and/or optionally at least one oxidation base optionally combined with at least one coupler, and, second, a composition comprising, in a cosmetically acceptable medium, at least one oxidizing agent, and then mixing them together at the time of use. Once these steps have been performed, the processes are carried out as mentioned above.

The disclosure also provides multi-compartment devices, comprising at least one compartment containing a composition comprising at least one direct dye of formula (I) or (I'), and at least one other compartment containing a composition comprising at least one oxidizing agent. The devices may be equipped with a means for applying the desired mixture to the hair, such as the devices described in patent FR-2 586 913.

It should be noted that the in the case where the compositions comprise at least one additional direct dye and/or at least one oxidation base optionally combined with at least one coupler, according to a first variant, these compounds are in the first compartment of the devices described above. According to another embodiment, the additional direct dye and/or the oxidation base/coupler are stored in a third compartment.

It is also possible to have an embodiment combining the two previous embodiments, in which the additional direct dye and/or the oxidation base and optionally the coupler would be partly in the first compartment, with the direct compound of formula (I) or (I'), and partly in a third compartment.

The invention is illustrated in greater detail by the examples described below. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

EXAMPLE 1

The following composition was prepared:

| | |
|---|---|
| Fluorescent dye (A) | $1.73 \times 10^{-2}$ mol/l |
| Distilled water | qs 100% |

Compound (A) has the following structure:

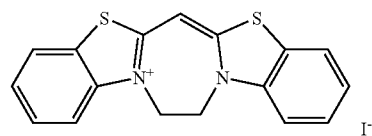

14-Dihydrobisbenzothiazolo[3,2-d:2',3'-g][1,4]diazepin-12-ium, iodide

The composition was applied to chestnut-brown hair (tone height of 4) for 20 minutes at room temperature. The bath ratio was set at 5. After dyeing, the locks were rinsed and dried.

A shampoo-fast lightening effect was obtained.

Furthermore, the composition was stable.

EXAMPLE 2

The following composition was prepared:

| | |
|---|---|
| Compound (B) | $10^{-3}$ mol % |
| Distilled water | qs 100% |

Compound (B) has the following structure:

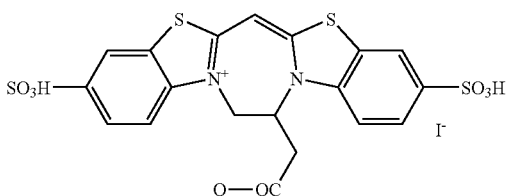

Internal salt of bisbenzoxazolo[3,2-d:2',3'-g][1,4]
diazepin-12-ium, 13-(carboxymethyl)-13,14-dihydro-2,10-disulfo The composition was applied to natural grey hair for 20 minutes at room temperature. The bath ratio was set at 5. After dyeing, the locks were rinsed and dried.

The yellow color obtained was shampoo-fast.

The composition was stable upon storage.

What is claimed is:

1. A composition comprising, in a cosmetically acceptable medium, at least one direct dye of formula (I) or (I'):

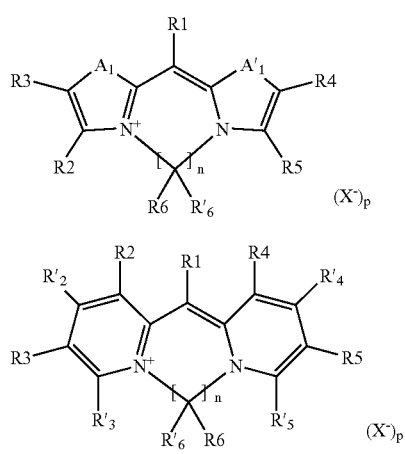

wherein:

$A_1$ and $A'_1$, which may be identical or different, are each chosen from oxygen, sulfur, and nitrogen substituted with a linear or branched $C_1$-$C_6$ alkyl radical, optionally substituted with one or more groups chosen from halo, hydroxyl; selenium, and $CR'_2$;

$R_1$, $R_6$ and $R'_6$, which may be identical or different, are each chosen from hydrogen; a linear, branched or cycloalkyl $C_1$-$C_{22}$ radical, optionally substituted with at least one hydroxyl group, at least one linear or branched $C_1$-$C_6$ alkoxy group, at least one $C_1$-$C_6$ cycloalkoxy group, or at least one $C_6$-$C_{30}$ aryl or aryloxy group optionally substituted with at least one sulfo group, with at least one carboxyl group or with at least one $C_1$-$C_6$ alkoxycarbonyl group; and a $C_6$-$C_{30}$ aryl radical;

$R_2$, $R'_2$, $R_3$, $R'_3$, $R_4$, $R'_4$, $R_5$ and $R'_5$, which may be identical or different, are each chosen from hydrogen; a linear or branched $C_1$-$C_{22}$ radical, optionally substituted with at least one hydroxyl, carboxyl, halo or sulfo radical; or $R_2$, $R'_2$, $R_3$ and $R'_3$, may optionally form in pairs with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, with at least one halogen atom, at least one sulfo radical, at least one carboxyl group, or at least one $C_6$-$C_{30}$ aryl radical;

$R_4$, $R'_4$, $R_5$ and $R'_5$, may optionally form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, with at least one halogen atom, with at least one sulfo radical, with at least one carboxyl group, or with at least one $C_6$-$C_{30}$ aryl radical;

$R_2$ and $R_6$, $R_5$ and $R_6$, $R'_3$ and $R_6$ and/or $R'_5$ and $R_6$ may optionally form a heteroaromatic ring;

or in formula (I'), $R_2$ and $R'_2$, $R_3$ and $R'_3$, $R_2$ and $R'_4$ and/or $R_5$ and $R'_5$ may form in pairs with the carbon atoms to which each is attached, an aromatic or heteroaromatic ring;

n is an integer ranging from 1 to 3;

p is an integer equal to 0 or 1; and $X^-$ is an organic or mineral anion;

wherein the at least one direct dye is not 8H-isoquino[2', 1':3,4]pyrimido[1,6-a]quinolin-7-ium, 8-phenyl, chloride;

and wherein the content of the at least one direct dye ranges from 0.01% to 20% by weight relative to the total weight of the composition.

2. The composition according to claim 1 wherein at least one of $R_1$, $R_6$ and $R'_6$ is a $C_1$-$C_6$ alkyl radical.

3. The composition according to claim 1 wherein at least one of $R_2$, $R'_2$, $R_3$, $R'_3$, $R_4$, $R'_4$, $R_5$ and $R'_5$ is a $C_1$-$C_{10}$ radical.

4. The composition according to claim 3 wherein at least one of $R_2$, $R'_2$, $R_3$, $R'_3$, $R_4$, $R'_4$, $R_5$ and $R'_5$ is a $C_1$-$C_6$ radical.

5. The composition according claim 1, wherein $R_1$, $R_6$ and $R'_6$, are chosen from hydrogen, a linear or branched $C_1$-$C_{22}$ alkyl radical, optionally substituted with at least one phenyl or phenyloxy group optionally substituted with at least one sulfo group, at least one carboxyl group, or at least one $C_1$-$C_6$ alkoxycarbonyl group; and a phenyl radical.

6. The composition according claim 5, wherein at least one of $R_1$, $R_6$ and $R'_6$ is a $C_1$-$C_6$ alkyl radical.

7. The composition according to claim 1, wherein $R_2$, $R'_2$, $R_3$ and $R'_3$ or $R_4$, $R'_4$, $R_5$ and $R'_5$ form in pairs, together with the carbon atoms to which each is attached, an aliphatic, heterocyclic, aromatic or heteroaromatic ring optionally fused to an identical or different aromatic or heteroaromatic ring; the an aliphatic, heterocyclic, aromatic or heteroaromatic ring being optionally substituted with at least one linear or branched $C_1$-$C_6$ alkyl radical optionally bearing a carboxyl group, at least one halogen atom, at least one sulfo radical, or with at least one carboxyl group.

8. The composition according to claim 1, wherein at least one of $R_2$, $R'_2$, $R_3$, $R'_3$, $R_4$, $R'_4$, $R_5$ and $R'_5$ is a hydrogen atom or a linear or branched $C_1$-$C_{22}$ alkyl radical.

9. The composition according to claim 8, wherein at least one of $R_2$, $R'_2$, $R_3$, $R'_3$, $R_4$, $R'_4$, $R_5$ and $R'_5$ is a linear or branched $C_1$-$C_{10}$ alkyl radical.

10. The composition according to claim 8, wherein at least one of $R_2$, $R'_2$, $R_3$, $R'_3$, $R_4$, $R'_4$, $R_5$ and $R'_5$ is a linear or branched $C_1$-$C_6$ alkyl radical.

11. The composition according to claim 8, wherein at least one $R_2$, $R'_2$, $R_3$, $R'_3$, $R_4$, $R'_4$, $R_5$ and $R'_5$ is a hydrogen atom or a methyl radical.

12. The composition according to claim 1, wherein $A_1$ is identical to $A'_1$.

13. The composition according to claim 1, wherein
the mineral anion is chosen from halides, sulfates, bisulfates, nitrates, phosphates, hydrogen phosphates, dihydrogen phosphates, carbonates, and bicarbonates; and
the organic anion is chosen from anions originating from salts of saturated or unsaturated, aromatic or non-aromatic sulfonic, sulfuric, mono- or polycarboxylic acids, optionally substituted with at least one hydroxyl radical, amino radical, or halogen atom.

14. The composition according to claim 13, wherein the anion is chosen from chloride, iodide, sulfate, methosulfate, and ethosulfate.

15. The composition according to claim 1, wherein the at least one direct dye is chosen from:
internal salt of bisnaphtho[2',3':4,5]thiazolo[3,2-d:2',3'-g][1,4]diazepin-15-ium, 16,17-dihydro-16,17-bis[2-(2-sulfophenyl)ethyl];
salt of bisnaphtho[2',3':4,5]thiazolo[3,2-d:2',3'-g[]1,4]diazepin-15-ium, 16,17-dihydro-16,17-bis(3-phenoxypropyl)-;
salt of bisbenzothiazolo[3,2-d:2',3'-g][1,4]diazepin-12-ium, 13,14-dihydro-2,10,13,14-tetraphenyl;
bisnaphth[2',3':4,5]oxazolo[3,2-d:2',3'-g][1,4]diazepin-15-ium, 16,17-dihydro-, chloride;
internal salt of bisbenzothiazolo[3,2-d:2',3'-g][1,4]diazepin-12-ium, 13-(carboxymethyl)-13,14-dihydro;
internal salt of bisbenzoxazolo[3,2-d:2',3'-g][1,4]diazepin-12-ium, 13-(carboxymethyl)-13,14-dihydro-2,10-disulfo;
internal salt of bisbenzothiazolo[3,2-d:2',3'-g][1,4]diazepin-12-ium, 13-(carboxymethyl)-13,14-dihydro-2,10-disulfo;
internal salt of bisbenzoxazolo[3,2-d:2',3'-g][1,4]diazepin-12-ium, 13,14-dihydro-13-(2-methoxy-2-oxoethyl)-2,10-disulfo;
internal salt of benzothiazolo[3',2':4,5][1,4]diazepino[7,1-b]benzoxazol-12-ium, 2-(carboxymethyl)-13,14-dihydro;
internal salt of bisbenzothiazolo[3,2-d:2',3'-g][1,4]diazepin-12-ium, 6-(5-carboxypentyl)-13,14-dihydro;
internal salt of benzothiazolo[3',2':4,5][1,4]diazepino[7,1-b]benzoxazol-12-ium, 2-carboxy-13,14-dihydro-3,9-disulfo;
1,4-dihydrobisbenzothiazolo[3,2-d:2',3'-g][1,4]diazepin-12-ium, iodide;
5h-bisbenzimidazo[1,2-d:2',1'-g][1,4]diazepinium, 2,3,9,10-tetrachloro-5,7-diethyl-13,14-dihydro-, iodide;
5h-bisbenzimidazo[1,2-d:2',1'-g][1,4]diazepinium, 2,3,9,10-tetrachloro-13,14-dihydro-5,7-bis(2,2,2-trifluoroethyl)-, tosylate;
5h-bisbenzimidazo[1,2-d:2',1'-g][1,4]diazepinium, 2,3,9,10-tetrachloro-13,14-dihydro-5,7-dimethyl, iodide;
6h-[1,4]diazepino[1'',7'':1,2;4'',5'':1',2']diimidazo[4,5-b:4',5'-b']diquinoxalinium, 6,8-diethyl-16,17-dihydro, perchlorate;
5h-bisbenzimidazo[1,2-d:2',1'-g][1,4]diazepinium, 5,7-diethyl-13,14-dihydro, iodide
salt of bisbenzimidazo[1,2-d:2',1'-g][1,4]diazepin-12-ium, 5,7,13,14-tetrahydro-5,7-dimethyl];
salt of [1,4]diazepino[7,1,2-cd:5,4,3-c'd']diindolizin-12-ium, 4,5,7,8-tetramethyl;
salt of [1,4]diazepino[7,1,2-cd:5,4,3-c'd']diindolizin-12-ium;
salt of bisbenzoxazolo[3,2-d:2',3'-g][1,4]diazepin-12-ium, 13,14-dihydro;
10h-pyrimido[1,6-f:3,4-f']diphenanthridin-9-ium, iodide;
13h-pyrido[1',2':3,4]pyrimido[1,6-a]quinolin-14-ium, iodide;
8h-isoquino[2',1':3,4]pyrimido[1,6-a]quinolin-7-ium, 8-cyclohexyl, chloride;
15h-pyrimido[1,6-a:3,4-a']diquinolin-14-ium, iodide;
6h-dipyrido[1,2-c:2',1'-f]pyrimidin-5-ium, iodide;
salt (example chloride) of 17h-dibenzo[f,f']pyrimido[1,6-a:3,4-a']diquinolin-16-ium;
15-phenyl-15h-pyrimido[1,6-a:3,4-a']diquinolin-14-ium, iodide;
15h-pyrimido[1,6-a:3,4-a']diquinolin-14-ium, 15,15-diphenyl, chloride;
15h-pyrimido[1,6-a:3,4-a']diquinolin-14-ium, chloride;
salt of 13h-pyrimido[6,1-b:4,3-b']bisbenzothiazol-12-ium;
13h-pyrimido[6,1-b:4,3-b']bisbenzothiazol-12-ium, 6-phenyl, iodide;
5h-dipyrrolo[1,2-c:2',1'-f]pyrimidin-4-ium, 1,3,7,9,10-pentamethyl, chloride;
salt of 5h-bisthiazolo[3,2-c:2',3'-f]pyrimidin-4-ium;
5h, 13h-pyrimido[1,6-a:3,4-a']bisbenzimidazolium, 2,3,9,10-tetrachloro-5,7-dimethyl, iodide;
6h, 12h-pyrimido[1,6-a:3,4-a']bisbenzimidazolium, 12,14-dimethyl-, perchlorate;
salt of 6h, 12h-pyrimido[1,6-a:3,4-a']bisbenzimidazolium, 12,14-dimethyl;
dipyrido[1,2-d:2',1'-g][1,4]diazepin-5-ium, 6,7-dihydro, bromide;
dipyrido[1,2-d:2',1'-g][1,4]diazepin-5-ium, 6,7-dihydro-2,4,9,11-tetraphenyl, perchlorate;
dipyrido[1,2-d:2',1'-g][1,4]diazepin-5-ium, 2,4,9,11-tetrakis(1,1-dimethylethyl)-6,7-dihydro, perchlorate;
[1,4]diazepino[1,7-a:4,5-a']diquinolin-14-ium, 15,16-dihydro, bromide;
6h, 14h-bisbenzimidazo[1,2-a:2',1'-d][1,5]diazocinium, 2,3,11,12-tetrachloro-7,8-dihydro-14,16-dimethyl, 4-methylbenzenesulfonate; and
salt of 6h-bisbenzothiazolo[3,2-a:2',3'-d][1,5]diazocin-5-ium, 7,8-dihydro.

16. The composition according to claim 15, wherein the at least one direct dye is a chloride salt.

17. The composition according to claim 1, wherein the content of the at least one direct dye ranges from 0.1% to 5% by weight relative to the total weight of the composition.

18. The composition according to claim 1, wherein the cosmetically acceptable medium comprises water or a mixture of water and at least one organic solvent.

19. The composition according to claim 1, further comprising at least one additional non-ionic, cationic or anionic direct dye.

20. The composition according to claim 19, wherein the at least one additional direct dye is chosen from nitrobenzene dyes, azo, anthraquinone, naphthoquinone or benzoquinone dyes, indigoid dyes, triarylmethane-based dyes, natural dyes, and mixtures thereof.

21. The composition according to claim 19, wherein the at least one additional direct dye ranges from 0.0005% to 12% by weight relative to the total weight of the composition.

22. The composition according to claim 1, further comprising at least one surfactant.

23. The composition according to claim 22, wherein the at least one surfactant is a non-ionic surfactant.

24. The composition according to claim 22, wherein the at least one surfactant ranges from 0.01% to 50% by weight relative to the total weight of the composition.

25. The composition according claim 1, further comprising at least one non-associative thickening polymer.

26. The composition according to claim 25, wherein the at least one non-associative thickening polymer is chosen from at least one of crosslinked acrylic acid homopolymers, crosslinked 2-acrylamido-2-methylpropanesulfonic acid homopolymers and crosslinked acrylamide copolymers thereof, ammonium acrylate homopolymers or copolymers of ammonium acrylate and acrylamide, nonionic guar gums, microbial biopolysaccharide gums, plant exudate gums, hydroxypropyl celluloses, carboxymethyl celluloses, and pectins alginate.

27. The composition according to claim 25, wherein the content of the at least one non-associative thickening polymer ranges from 0.01% to 10% by weight relative to the weight of the composition.

28. The composition according to claim 26, wherein the content of the at least one non-associative thickening polymer ranges from 0.1% to 5% by weight relative to the weight of the composition.

29. The composition according claim 1, further comprising at least one associative thickening polymer.

30. The composition according to claim 29, wherein the at least one associative thickening polymer is chosen from associative polyurethanes, associative unsaturated polyacids, associative aminoplast-ethers, crosslinked 2-acryl-amido-2-methylpropanesulfonic acid homopolymers and crosslinked acrylamide copolymers thereof, associative polymers or copolymers comprising at least one ethylenically unsaturated monomer containing a sulfonic group, and mixtures thereof.

31. The composition according to claim 30, wherein the at least one associative thickening polymer is chosen from cationic or nonionic, associative cellulose derivatives.

32. The composition according to claim 31, wherein the at least one associative thickening polymer is chosen from cationic or nonionic, associative vinyl lactams.

33. The composition according to claim 29, wherein the content of the at least one associative thickening polymer ranges from 0.01% to 10% by weight relative to the weight of the composition.

34. The composition according to claim 33, wherein the content of the at least one associative thickening polymer ranges from 0.1% to 5% by weight relative to the weight of the composition.

35. The composition according claim 1, further comprising at least one adjuvant chosen from anionic, cationic, nonionic, amphoteric, zwitterionic polymers and mixtures thereof; mineral thickeners; antioxidants; penetrating agents; sequestering agents; fragrances; buffers; dispersants; conditioners; film-forming agents; ceramides; preserving agents; stabilizers; and opacifiers.

36. The composition according to claim 1, in the form of a coloring shampoo.

37. The composition according to claim 1, further comprising at least one oxidation base optionally combined with at least one coupler.

38. The composition according to claim 37, wherein the at least one oxidation base is chosen from para-phenylenediamines, bis-phenylalkylenediamines, para-aminophenols, ortho-aminophenols, heterocyclic bases, and acid or alkaline addition salts.

39. The composition according to claim 37, wherein the at least one oxidation base ranges from 0.0005% to 12% by weight relative to the total weight of the composition.

40. The composition according to claim 37, wherein the at least one coupler is chosen from meta-phenylenediamines, meta-aminophenols, meta-diphenols, heterocyclic couplers, and acid or alkaline addition salts thereof.

41. The composition according to claim 37, wherein the at least one coupler ranges from 0.0001% to 10% by weight relative to the total weight of dye composition.

42. The composition according to claim 1, further comprising at least one oxidizing agent.

43. The composition according to claim 42, wherein the at least one oxidizing agent is chosen from hydrogen peroxide, urea peroxide, alkali metal bromates, persalts, and enzymes.

44. The composition according to claim 43, wherein the at least one oxidizing agent is a persalt chosen from perborates and persulfates.

45. A process for treating keratin fibers, comprising:
applying a composition to fibers that are wet or dry for a time sufficient to develop a coloration,
rinsing the fibers;
optionally washing the fibers with shampoo and rinsing the fibers a second time; and
drying the fibers leaving the fibers to dry;
wherein the composition comprises, in a cosmetically acceptable medium, at least one direct dye of formula (I) or (I'):

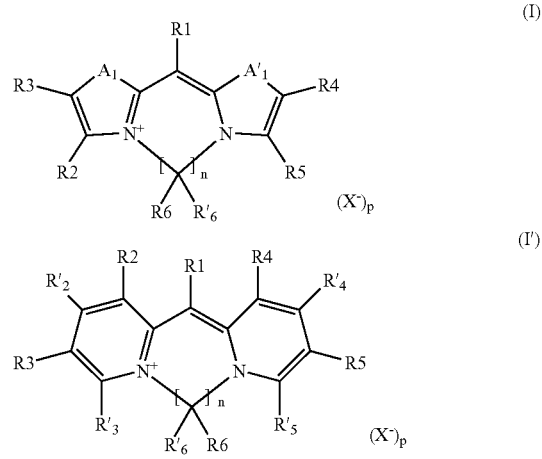

wherein:
$A_1$ and $A'_1$, which may be identical or different, are each chosen from oxygen, sulfur, and nitrogen substituted with a linear or branched $C_1$-$C_6$ alkyl radical, optionally substituted with one or more groups chosen from halo, hydroxyl; selenium, and $CR'_2$;

$R_1$, $R_6$ and $R'_6$, which may be identical or different, are each chosen from hydrogen; a linear, branched or cycloalkyl $C_1$-$C_{22}$ radical, optionally substituted with at least one hydroxyl group, at least one linear or branched $C_1$-$C_6$ alkoxy group, at least one $C_1$-$C_6$ cycloalkoxy group, at least one $C_6$-$C_{30}$ aryl or aryloxy group optionally substituted with at least one sulfo group, at least one carboxyl group or at least one $C_1$-$C_6$ alkoxycarbonyl group; and a $C_6$-$C_{30}$ aryl radical;

$R_2$, $R'_2$, $R_3$, $R'_3$, $R_4$, $R'_4$, $R_5$ and $R'_5$, which may be identical or different, are each chosen from hydrogen; a linear or branched $C_1$-$C_{22}$ radical, optionally substituted with at least one hydroxyl, carboxyl, halo or sulfo radical; or $R_2$, $R'_2$, $R_3$ and $R'_3$, may optionally form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, at least one halogen atom, at least one sulfo radical, at least one carboxyl group, or at least one $C_6$-$C_{30}$ aryl radical;

$R_4$, $R'_4$, $R_5$ and $R'_5$, may optionally form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, at least one halogen atom, at least one sulfo radical, at least one carboxyl group, or at least one $C_6$-$C_{30}$ aryl radical;

$R_2$ and $R_6$, $R_5$ and $R_6$, $R'_3$ and $R_6$ and/or $R'_5$ and $R_6$ may optionally form a heteroaromatic ring;

or in formula (I'), $R_2$ and $R'_2$, $R_3$ and $R'_3$, $R_2$ and $R'_4$ and/or $R_5$ and $R'_5$ may form in pairs with the carbon atoms to which each is attached, an aromatic or heteroaromatic ring;

n is an integer ranging from 1 to 3;

p is an integer equal to 0 or 1; and $X^-$ is an organic or mineral anion;

wherein the at least one direct dye is not 8H-isoquino[2', 1':3,4]pyrimido[1,6-a]quinolin-7-ium, 8-phenyl, chloride.

46. The process of claim 45, wherein the keratin fibers are human keratin fibers.

47. The process of claim 45, wherein the keratin fibers are not rinsed a second time.

48. A multi-compartment device for dyeing and lightening the hair, comprising:
a first compartment comprising a composition comprising at least one oxidizing agent; and
at least one second compartment containing a composition comprising in a cosmetically acceptable medium, at least one direct dye of formula (I) or (I'):

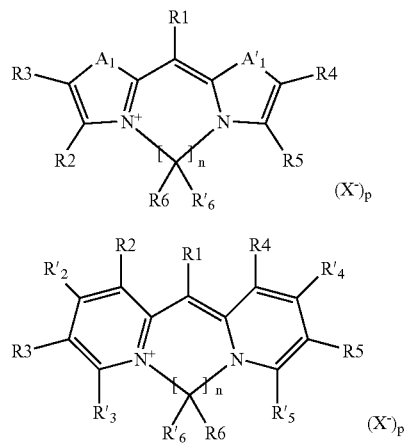

wherein:

$A_1$ and $A'_1$, which may be identical or different, are each chosen from oxygen, sulfur, and nitrogen substituted with a linear or branched $C_1$-$C_6$ alkyl radical, optionally substituted with one or more groups chosen from halo, hydroxyl; selenium, and $CR'_2$;

$R_1$, $R_6$ and $R'_6$, which may be identical or different, are each chosen from hydrogen; a linear, branched or cycloalkyl $C_1$-$C_{22}$ radical, optionally substituted with at least one hydroxyl group, at least one linear or branched $C_1$-$C_6$ alkoxy group, at least one $C_1$-$C_6$ cycloalkoxy group, or at least one $C_6$-$C_{30}$ aryl or aryloxy group optionally substituted with at least one sulfo group, with at least one carboxyl group or at least one $C_1$-$C_6$ alkoxycarbonyl group; and a $C_6$-$C_{30}$ aryl radical;

$R_2$, $R'_2$, $R_3$, $R'_3$, $R_4$, $R'_4$, $R_5$ and $R'_5$, which may be identical or different, are each chosen from hydrogen; a linear or branched $C_1$-$C_{22}$ radical, optionally substituted with at least one hydroxyl, carboxyl, halo or sulfo radical; or $R_2$, $R'_2$, $R_3$ and $R'_3$, may optionally form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, with at least one halogen atom, at least one sulfo radical, at least one carboxyl group, or at least one $C_6$-$C_{30}$ aryl radical;

$R_4$, $R'_4$, $R_5$ and $R'_5$, may optionally form in pairs together with the carbon atoms to which each is attached, an aliphatic, heterocyclic, aromatic or heteroaromatic ring optionally fused to a second aromatic or heteroaromatic ring; the aliphatic, heterocyclic, aromatic or heteroaromatic ring optionally substituted with at least one linear or branched $C_1$-$C_4$ alkyl radical optionally bearing a carboxyl group, with at least one halogen atom, at least one sulfo radical, at least one carboxyl group, or at least one $C_6$-$C_{30}$ aryl radical;

$R_2$ and $R_6$, $R_5$ and $R_6$, $R'_3$ and $R_6$ and/or $R'_5$ and $R_6$ may optionally form an heteroaromatic ring;

or in formula (I'), $R_2$ and $R'_2$, $R_3$ and $R'_3$, $R_2$ and $R'_4$ and/or $R_5$ and $R'_5$ may form in pairs with the carbon atoms to which each is attached, an aromatic or heteroaromatic ring;

n is an integer ranging from 1 to 3;

p is an integer equal to 0 or 1; and $X^-$ is an organic or mineral anion.

* * * * *

UNITED STATES PATENT AND TRADEMARK OFFICE
CERTIFICATE OF CORRECTION

| | | |
|---|---|---|
| PATENT NO. | : 7,419,511 B2 | Page 1 of 1 |
| APPLICATION NO. | : 11/223961 | |
| DATED | : September 2, 2008 | |
| INVENTOR(S) | : Lagrange | |

It is certified that error appears in the above-identified patent and that said Letters Patent is hereby corrected as shown below:

In Claim 15, column 45, line 23, "[]" should read --][--.

Signed and Sealed this

Eleventh Day of November, 2008

JON W. DUDAS
*Director of the United States Patent and Trademark Office*